(12) United States Patent
Yoon et al.

(10) Patent No.: US 10,479,822 B2
(45) Date of Patent: Nov. 19, 2019

(54) PHARMACEUTICAL COMPOSITIONS CONTAINING, AS ACTIVE INGREDIENT, GRANULOCYTE-COLONY STIMULATING FACTOR MUTANT PROTEIN OR TRANSFERRIN FUSION PROTEIN THEREOF

(71) Applicant: Supex Bnp Co., Ltd., Gyeonggi-do (KR)

(72) Inventors: Jeong-Hyeok Yoon, Gyeonggi-do (KR); Byung-Ha Chang, Gyeonggi-do (KR); Bong-Seok Jin, Gyeonggi-do (KR); Ji Young Bae, Seoul (KR); Soon Nam Kim, Gyeonggi-do (KR); Kyeong Su Park, Gyeonggi-do (KR); Yeong kyu Park, Seoul (KR); Hanjo Kim, Seoul (KR); Youngju Seo, Seoul (KR); Wooseong Jeong, Seoul (KR); KyungTae Kang, Gyeonggi-do (KR)

(73) Assignee: SUPEX BNP CO., LTD., Gyeonggi-Do (KR)

( * ) Notice: Subject to any disclaimer, the term of this patent is extended or adjusted under 35 U.S.C. 154(b) by 161 days.

(21) Appl. No.: 15/327,838

(22) PCT Filed: Nov. 21, 2014

(86) PCT No.: PCT/KR2014/011269
§ 371 (c)(1),
(2) Date: Jan. 20, 2017

(87) PCT Pub. No.: WO2016/013725
PCT Pub. Date: Jan. 28, 2016

(65) Prior Publication Data
US 2017/0218038 A1  Aug. 3, 2017

(30) Foreign Application Priority Data

Jul. 23, 2014 (KR) .......... 10-2014-0093260
Oct. 13, 2014 (KR) .......... 10-2014-0137414

(51) Int. Cl.
| C07K 14/535 | (2006.01) |
| C07K 14/79 | (2006.01) |
| A61K 38/00 | (2006.01) |
| C07K 1/00 | (2006.01) |

(52) U.S. Cl.
CPC .......... *C07K 14/535* (2013.01); *C07K 14/79* (2013.01); *A61K 38/00* (2013.01); *C07K 2319/00* (2013.01); *C07K 2319/31* (2013.01)

(58) Field of Classification Search
None
See application file for complete search history.

(56) References Cited

U.S. PATENT DOCUMENTS

| 8,188,032 B2 * | 5/2012 | Shen ............... A61K 38/193 |
| | | 514/1.1 |
| 2011/0020266 A1 * | 1/2011 | Nissen ............... C07K 14/53 |
| | | 424/85.1 |

FOREIGN PATENT DOCUMENTS

| KR | 1020010009171 A | 2/2001 |
| KR | 1020040084884 A | 10/2004 |
| KR | 1020120047338 A | 5/2012 |
| WO | 200151510 A2 | 7/2001 |
| WO | 2005034877 A2 | 4/2005 |
| WO | 2009086132 A2 | 7/2009 |

OTHER PUBLICATIONS

Bai Yun et al: "Recombinant granulocyte colony-stimulating factortransferrin fusion protein as an oral myelopoietic agent", Proceedings National Academy of Sciences PNAS, National Academy of Sciences, May 17, 2005 (May 17, 2005), pp. 7292-7296, vol. 102, No. 20, US.
Shyu Woei-Cherng et al: "Granulocyte colony-stimulating factor for acute ischemic stroke: a randomized controlled trial", CMAJ. Canadian Medical Association Journal, The Association, Ottawa, Mar. 28, 2006 (Mar. 28, 2006), pp. 927-933, vol. 174, No. 7, CA.
Rasmus Sejersten Ripa: "Granulocyte-colony stimulating factor therapy to induce neovascularization in ischemic heart diseaseo", Danish Medical Journal B4411, Aug. 1, 2011 (Aug. 1. 2011 ), pp. 1-34, vol. 59, No. 3, DK.
International Search Report, Korean Search Authority, PCT/KR2014/011269, dated Apr. 3, 2015.

* cited by examiner

Primary Examiner — Joanne Hama
Assistant Examiner — Jegatheesan Seharaseyon
(74) Attorney, Agent, or Firm — Workman Nydegger

(57) ABSTRACT

The present invention relates to a fusion protein in which transferrin is peptide-bonded to a terminal of a granulocyte-colony stimulating factor (G-CSF) protein or a G-CSF mutant protein in which the 116$^{th}$ threonine is substituted with cysteine in the amino acid sequence of the G-CSF. Specifically, the granulocyte-colony stimulating factor (G-CSF) mutant protein of the present invention or the transferrin fusion protein thereof displays a significantly increased specific activity and blood stability, compared with the conventional human G-CSF, and has a higher purification efficiency than the conventional PEGylated G-CSF characterized by the extended half-life, so that it can be advantageously used for preventing or treating ischemic diseases or neutropenia.

11 Claims, 12 Drawing Sheets
Specification includes a Sequence Listing.

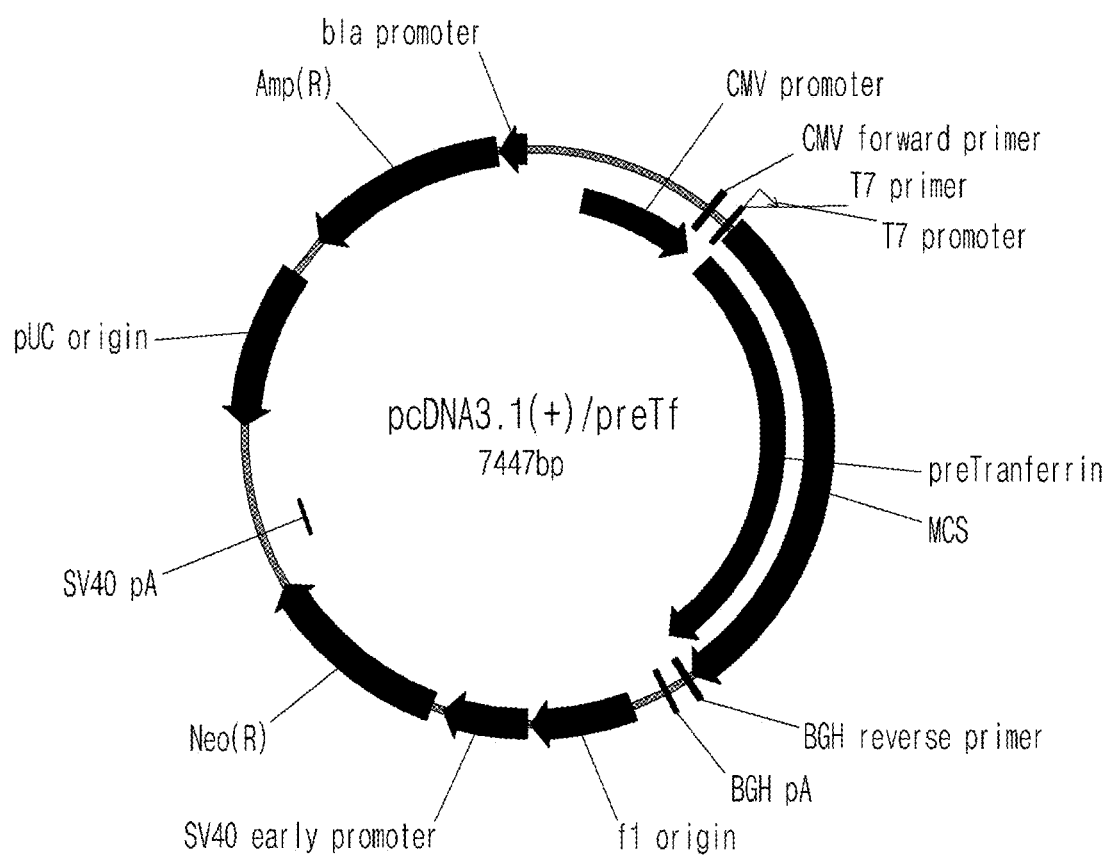
[Figure 1]

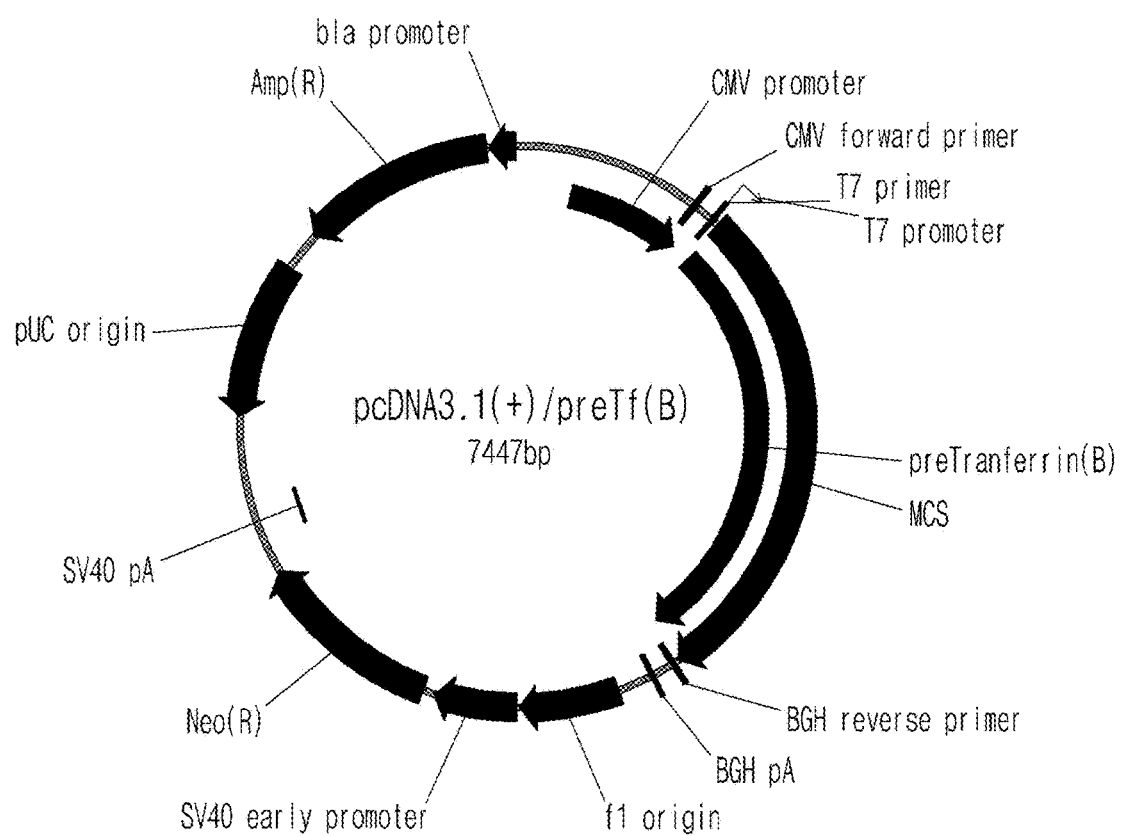
[Figure 2]

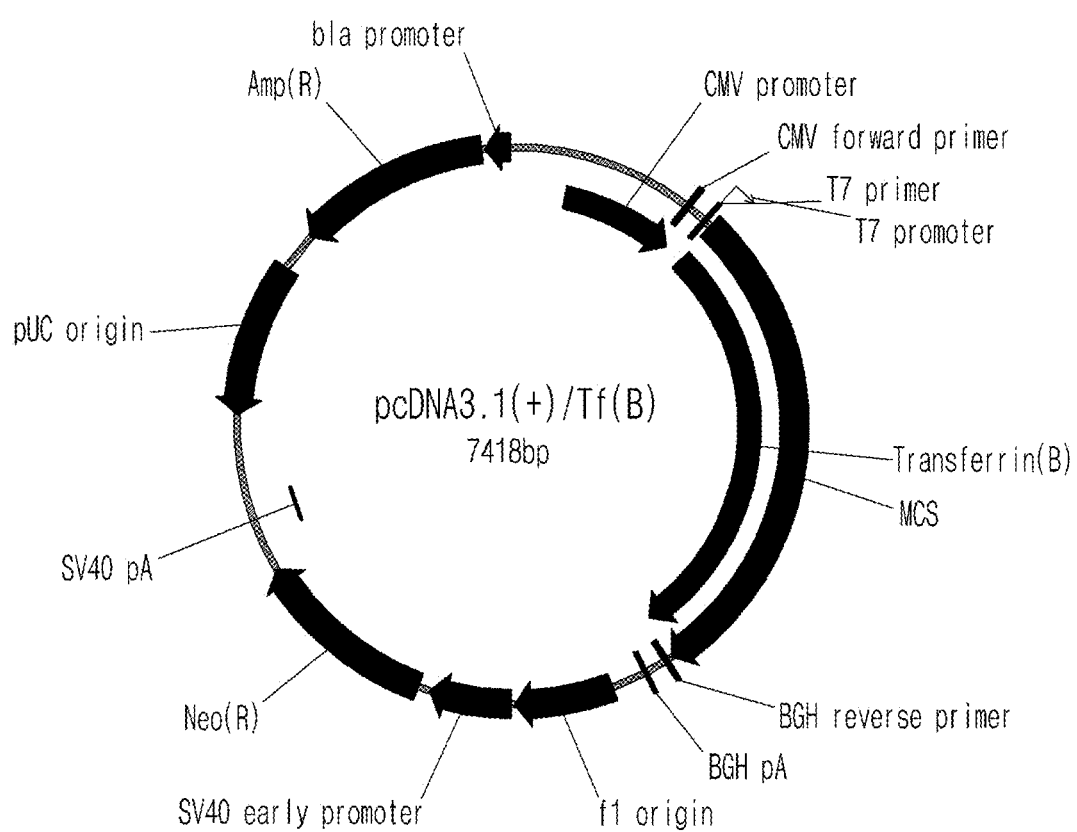
[Figure 3]

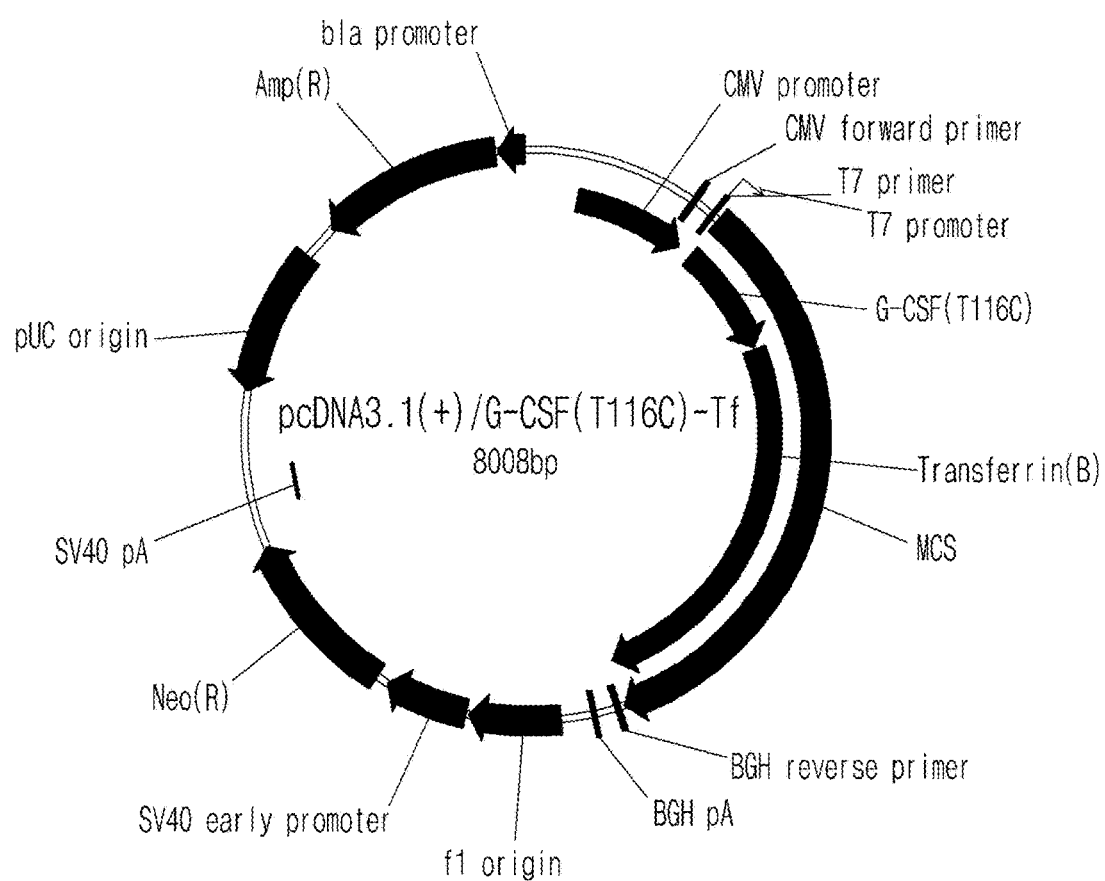
[Figure 4]

[Figure 5]
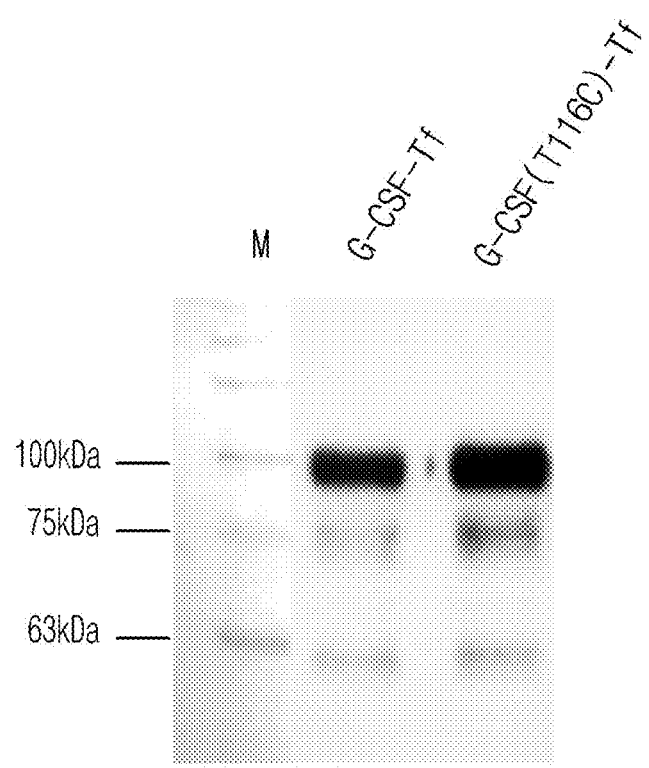

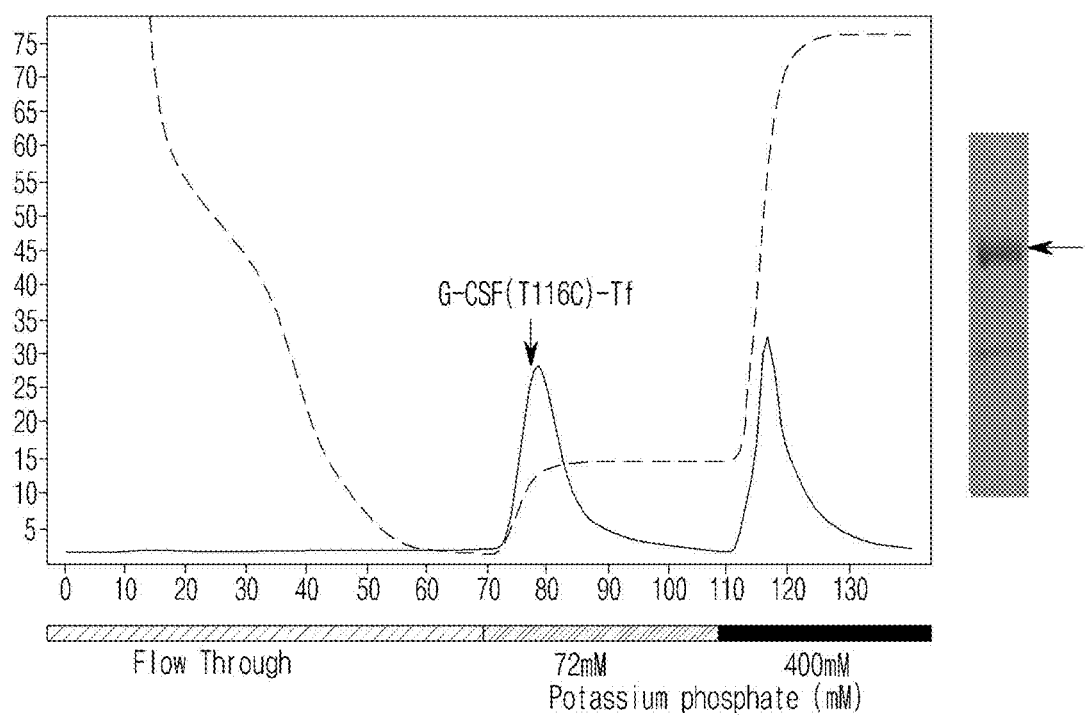
[Figure 6]

[Figure 7]
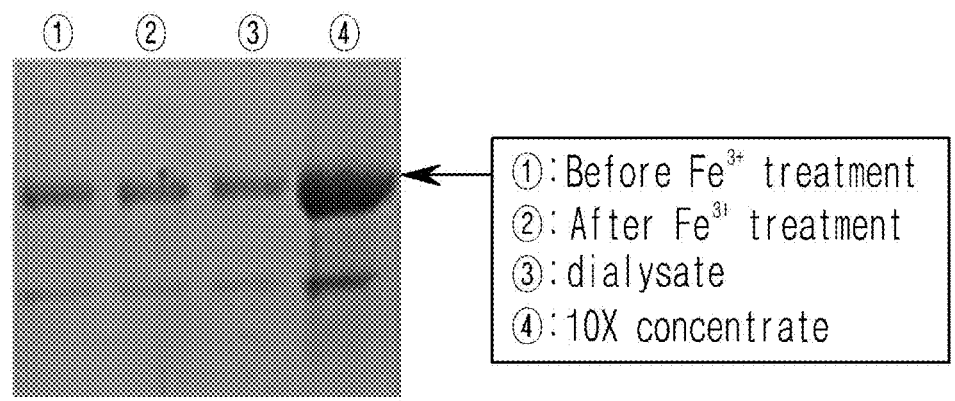

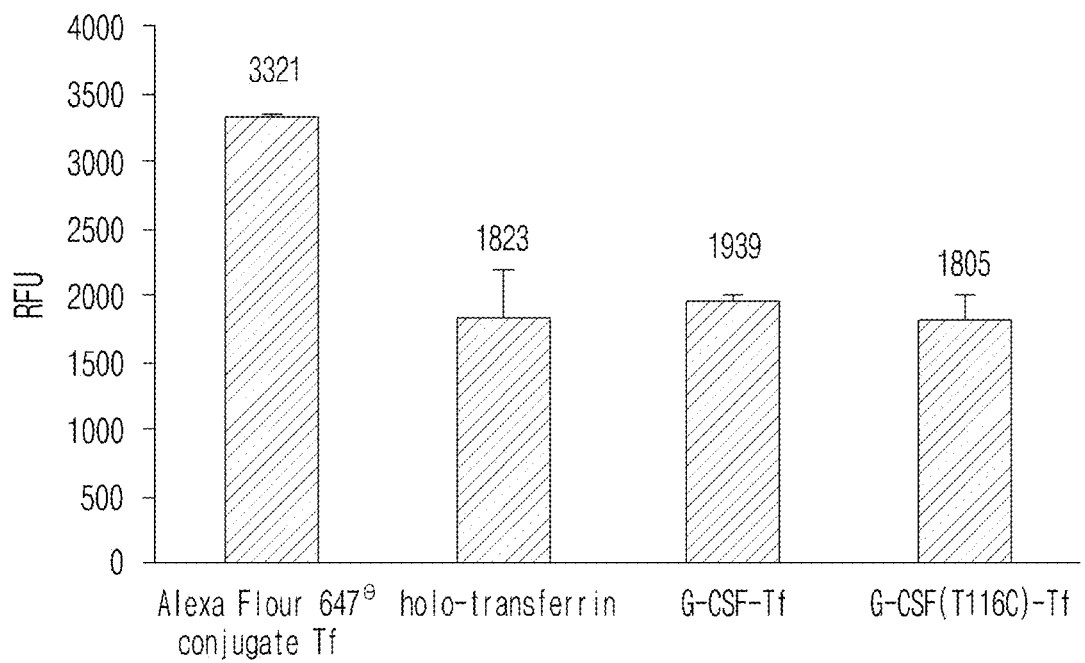
[Figure 8]

[Figure 9]
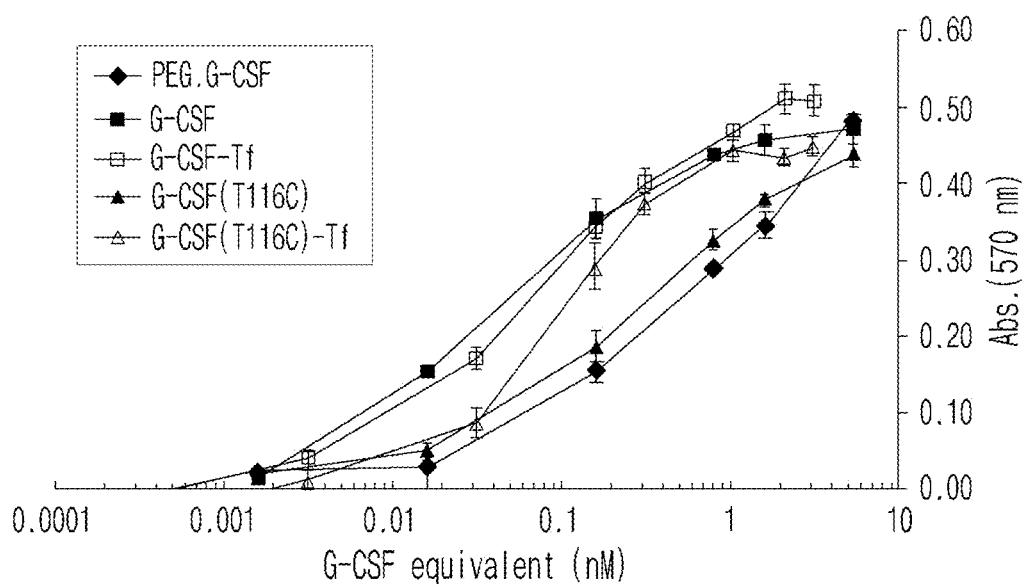

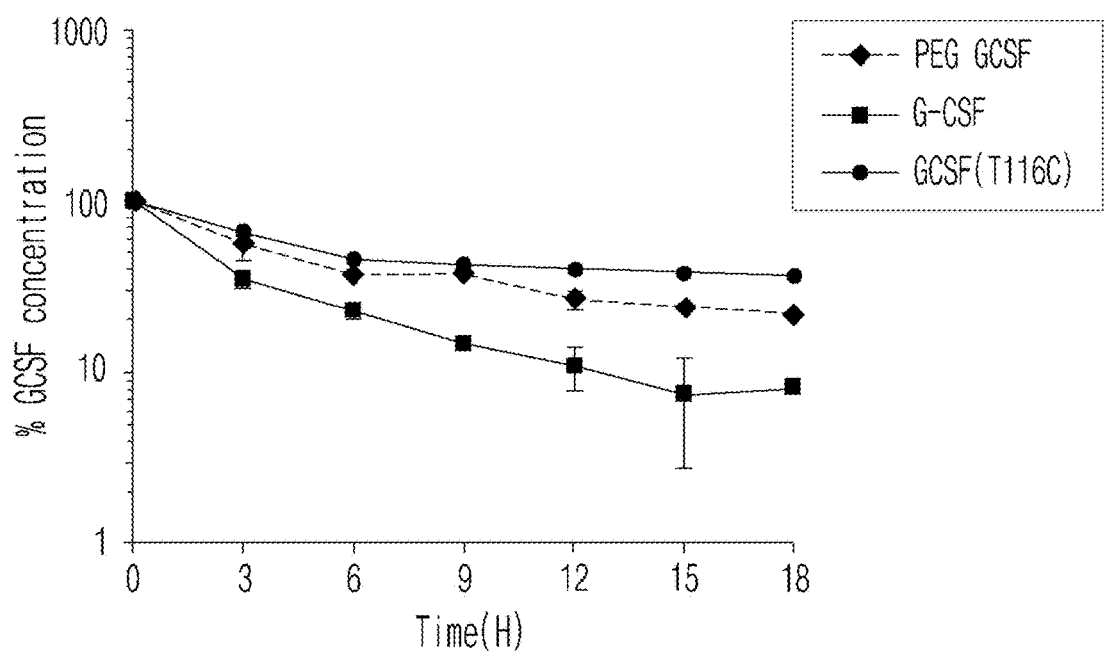
[Figure 10]

[Figure 11]
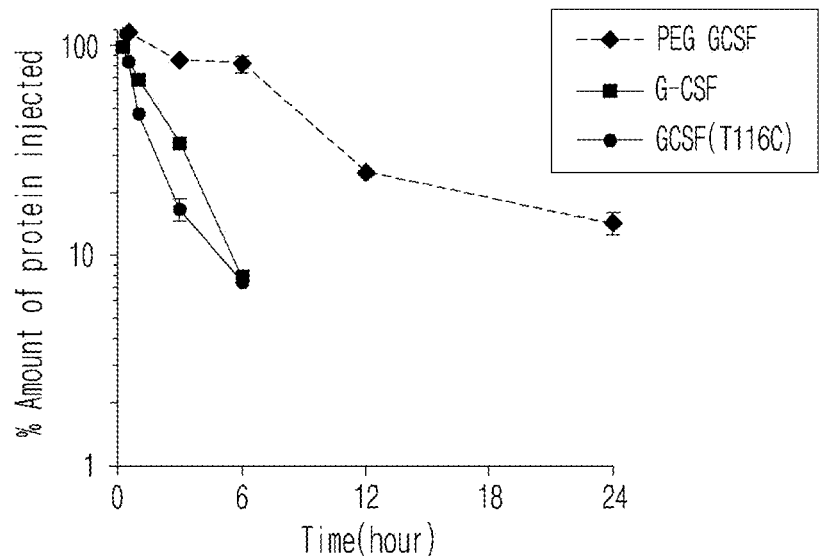
(a)
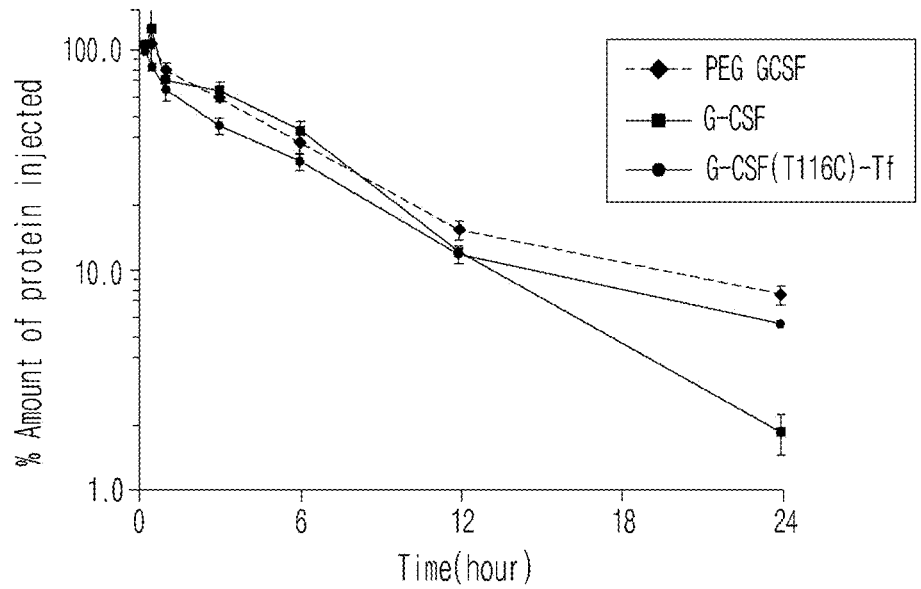
(b)
| Parameter(H) | G-CSF | G-CSF(T116C) | PEG. G-CSF | G-CSF-Tf | G-CSF(T116C)-Tf |
|---|---|---|---|---|---|
| $t_{1/2}$ | 1.88 | 1.84 | 6.77 | 3.95 | 6.50 |
(c)

[Figure 12]
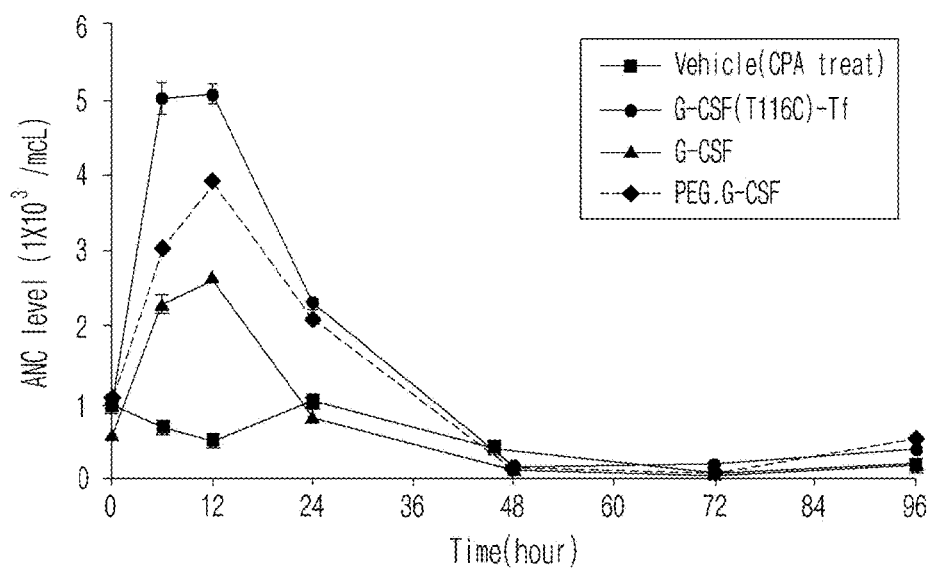
(a)
|  | $T_{max}$ (h) | $C_{max}$ (x10³ cells μL⁻¹) | $AUC_{0-t}$ (x10³ cells μL⁻¹ h⁻¹) |
|---|---|---|---|
| G-CSF | 12.00 | 2.66 | 56.11 |
| G-CSF(T116C)-Tf | 12.00 | 5.08 | 122.28 |
| PEG.G-CSF | 12.00 | 3.94 | 96.36 |
(b)

SEQUENCE LISTING

```
<160> NUMBER OF SEQ ID NOS: 21

<210> SEQ ID NO 1
<211> LENGTH: 174
<212> TYPE: PRT
<213> ORGANISM: Homo sapiens

<400> SEQUENCE: 1

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30
```

```
Glu Lys Leu Cys Ala Thr Tyr Lys Leu Cys His Pro Glu Leu Val
        35                  40                  45

Leu Leu Gly His Ser Leu Gly Ile Pro Trp Ala Pro Leu Ser Ser Cys
 50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 2
<211> LENGTH: 679
<212> TYPE: PRT
<213> ORGANISM: Homo sapiens

<400> SEQUENCE: 2

Val Pro Asp Lys Thr Val Arg Trp Cys Ala Val Ser Glu His Glu Ala
 1               5                  10                  15

Thr Lys Cys Gln Ser Phe Arg Asp His Met Lys Ser Val Ile Pro Ser
             20                  25                  30

Asp Gly Pro Ser Val Ala Cys Val Lys Lys Ala Ser Tyr Leu Asp Cys
         35                  40                  45

Ile Arg Ala Ile Ala Ala Asn Glu Ala Asp Ala Val Thr Leu Asp Ala
     50                  55                  60

Gly Leu Val Tyr Asp Ala Tyr Leu Ala Pro Asn Asn Leu Lys Pro Val
 65                  70                  75                  80

Val Ala Glu Phe Tyr Gly Ser Lys Glu Asp Pro Gln Thr Phe Tyr Tyr
                 85                  90                  95

Ala Val Ala Val Val Lys Lys Asp Ser Gly Phe Gln Met Asn Gln Leu
            100                 105                 110

Arg Gly Lys Lys Ser Cys His Thr Gly Leu Gly Arg Ser Ala Gly Trp
            115                 120                 125

Asn Ile Pro Ile Gly Leu Leu Tyr Cys Asp Leu Pro Glu Pro Arg Lys
    130                 135                 140

Pro Leu Glu Lys Ala Val Ala Asn Phe Phe Ser Gly Ser Cys Ala Pro
145                 150                 155                 160

Cys Ala Asp Gly Thr Asp Phe Pro Gln Leu Cys Gln Leu Cys Pro Gly
                165                 170                 175

Cys Gly Cys Ser Thr Leu Asn Gln Tyr Phe Gly Tyr Ser Gly Ala Phe
            180                 185                 190

Lys Cys Leu Lys Asp Gly Ala Gly Asp Val Ala Phe Val Lys His Ser
            195                 200                 205

Thr Ile Phe Glu Asn Leu Ala Asn Lys Ala Asp Arg Asp Gln Tyr Glu
    210                 215                 220

Leu Leu Cys Leu Asp Asn Thr Arg Lys Pro Val Asp Glu Tyr Lys Asp
```

-continued

```
            225                 230                 235                 240
Cys His Leu Ala Gln Val Pro Ser His Thr Val Ala Arg Ser Met
                    245                 250                 255
Gly Gly Lys Glu Asp Leu Ile Trp Glu Leu Leu Asn Gln Ala Gln Glu
            260                 265                 270
His Phe Gly Lys Asp Lys Ser Lys Glu Phe Gln Leu Phe Ser Ser Pro
                275                 280                 285
His Gly Lys Asp Leu Leu Phe Lys Asp Ser Ala His Gly Phe Leu Lys
            290                 295                 300
Val Pro Pro Arg Met Asp Ala Lys Met Tyr Leu Gly Tyr Glu Tyr Val
305                 310                 315                 320
Thr Ala Ile Arg Asn Leu Arg Glu Gly Thr Cys Pro Glu Ala Pro Thr
                    325                 330                 335
Asp Glu Cys Lys Pro Val Lys Trp Cys Ala Leu Ser His His Glu Arg
                340                 345                 350
Leu Lys Cys Asp Glu Trp Ser Val Asn Ser Val Gly Lys Ile Glu Cys
            355                 360                 365
Val Ser Ala Glu Thr Thr Glu Asp Cys Ile Ala Lys Ile Met Asn Gly
        370                 375                 380
Glu Ala Asp Ala Met Ser Leu Asp Gly Gly Phe Val Tyr Ile Ala Gly
385                 390                 395                 400
Lys Cys Gly Leu Val Pro Val Leu Ala Glu Asn Tyr Asn Lys Ser Asp
                    405                 410                 415
Asn Cys Glu Asp Thr Pro Glu Ala Gly Tyr Phe Ala Val Ala Val Val
                420                 425                 430
Lys Lys Ser Ala Ser Asp Leu Thr Trp Asp Asn Leu Lys Gly Lys Lys
            435                 440                 445
Ser Cys His Thr Ala Val Gly Arg Thr Ala Gly Trp Asn Ile Pro Met
        450                 455                 460
Gly Leu Leu Tyr Asn Lys Ile Asn His Cys Arg Phe Asp Glu Phe Phe
465                 470                 475                 480
Ser Glu Gly Cys Ala Pro Gly Ser Lys Lys Asp Ser Ser Leu Cys Lys
                    485                 490                 495
Leu Cys Met Gly Ser Gly Leu Asn Leu Cys Glu Pro Asn Asn Lys Glu
                500                 505                 510
Gly Tyr Tyr Gly Tyr Thr Gly Ala Phe Arg Cys Leu Val Glu Lys Gly
            515                 520                 525
Asp Val Ala Phe Val Lys His Gln Thr Val Pro Gln Asn Thr Gly Gly
        530                 535                 540
Lys Asn Pro Asp Pro Trp Ala Lys Asn Leu Asn Glu Lys Asp Tyr Glu
545                 550                 555                 560
Leu Leu Cys Leu Asp Gly Thr Arg Lys Pro Val Glu Glu Tyr Ala Asn
                    565                 570                 575
Cys His Leu Ala Arg Ala Pro Asn His Ala Val Val Thr Arg Lys Asp
                580                 585                 590
Lys Glu Ala Cys Val His Lys Ile Leu Arg Gln Gln Gln His Leu Phe
            595                 600                 605
Gly Ser Asn Val Thr Asp Cys Ser Gly Asn Phe Cys Leu Phe Arg Ser
        610                 615                 620
Glu Thr Lys Asp Leu Leu Phe Arg Asp Asp Thr Val Cys Leu Ala Lys
625                 630                 635                 640
Leu His Asp Arg Asn Thr Tyr Glu Lys Tyr Leu Gly Glu Glu Tyr Val
                    645                 650                 655
```

```
Lys Ala Val Gly Asn Leu Arg Lys Cys Ser Thr Ser Ser Leu Leu Glu
            660                 665                 670

Ala Cys Thr Phe Arg Arg Pro
            675
```

<210> SEQ ID NO 3
<211> LENGTH: 174
<212> TYPE: PRT
<213> ORGANISM: Homo sapiens

<400> SEQUENCE: 3

```
Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Cys Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

<210> SEQ ID NO 4
<211> LENGTH: 855
<212> TYPE: PRT
<213> ORGANISM: Homo sapiens

<400> SEQUENCE: 4

```
Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125
```

```
Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro Gly Ser
                165                 170                 175

Val Pro Asp Lys Thr Val Arg Trp Cys Ala Val Ser Glu His Glu Ala
            180                 185                 190

Thr Lys Cys Gln Ser Phe Arg Asp His Met Lys Ser Val Ile Pro Ser
        195                 200                 205

Asp Gly Pro Ser Val Ala Cys Val Lys Lys Ala Ser Tyr Leu Asp Cys
    210                 215                 220

Ile Arg Ala Ile Ala Ala Asn Glu Ala Asp Ala Val Thr Leu Asp Ala
225                 230                 235                 240

Gly Leu Val Tyr Asp Ala Tyr Leu Ala Pro Asn Asn Leu Lys Pro Val
                245                 250                 255

Val Ala Glu Phe Tyr Gly Ser Lys Glu Asp Pro Gln Thr Phe Tyr Tyr
            260                 265                 270

Ala Val Ala Val Val Lys Lys Asp Ser Gly Phe Gln Met Asn Gln Leu
        275                 280                 285

Arg Gly Lys Lys Ser Cys His Thr Gly Leu Gly Arg Ser Ala Gly Trp
    290                 295                 300

Asn Ile Pro Ile Gly Leu Leu Tyr Cys Asp Leu Pro Glu Pro Arg Lys
305                 310                 315                 320

Pro Leu Glu Lys Ala Val Ala Asn Phe Phe Ser Gly Ser Cys Ala Pro
                325                 330                 335

Cys Ala Asp Gly Thr Asp Phe Pro Gln Leu Cys Gln Leu Cys Pro Gly
            340                 345                 350

Cys Gly Cys Ser Thr Leu Asn Gln Tyr Phe Gly Tyr Ser Gly Ala Phe
        355                 360                 365

Lys Cys Leu Lys Asp Gly Ala Gly Asp Val Ala Phe Val Lys His Ser
    370                 375                 380

Thr Ile Phe Glu Asn Leu Ala Asn Lys Ala Asp Arg Asp Gln Tyr Glu
385                 390                 395                 400

Leu Leu Cys Leu Asp Asn Thr Arg Lys Pro Val Asp Glu Tyr Lys Asp
                405                 410                 415

Cys His Leu Ala Gln Val Pro Ser His Thr Val Val Ala Arg Ser Met
            420                 425                 430

Gly Gly Lys Glu Asp Leu Ile Trp Glu Leu Leu Asn Gln Ala Gln Glu
        435                 440                 445

His Phe Gly Lys Asp Lys Ser Lys Glu Phe Gln Leu Phe Ser Ser Pro
    450                 455                 460

His Gly Lys Asp Leu Leu Phe Lys Asp Ser Ala His Gly Phe Leu Lys
465                 470                 475                 480

Val Pro Pro Arg Met Asp Ala Lys Met Tyr Leu Gly Tyr Glu Tyr Val
                485                 490                 495

Thr Ala Ile Arg Asn Leu Arg Glu Gly Thr Cys Pro Glu Ala Pro Thr
            500                 505                 510

Asp Glu Cys Lys Pro Val Lys Trp Cys Ala Leu Ser His His Glu Arg
        515                 520                 525

Leu Lys Cys Asp Glu Trp Ser Val Asn Ser Val Gly Lys Ile Glu Cys
    530                 535                 540
```

Val Ser Ala Glu Thr Thr Glu Asp Cys Ile Ala Lys Ile Met Asn Gly
545                 550                 555                 560

Glu Ala Asp Ala Met Ser Leu Asp Gly Gly Phe Val Tyr Ile Ala Gly
            565                 570                 575

Lys Cys Gly Leu Val Pro Val Leu Ala Glu Asn Tyr Asn Lys Ser Asp
        580                 585                 590

Asn Cys Glu Asp Thr Pro Glu Ala Gly Tyr Phe Ala Val Ala Val Val
    595                 600                 605

Lys Lys Ser Ala Ser Asp Leu Thr Trp Asp Asn Leu Lys Gly Lys Lys
610                 615                 620

Ser Cys His Thr Ala Val Gly Arg Thr Ala Gly Trp Asn Ile Pro Met
625                 630                 635                 640

Gly Leu Leu Tyr Asn Lys Ile Asn His Cys Arg Phe Asp Glu Phe Phe
            645                 650                 655

Ser Glu Gly Cys Ala Pro Gly Ser Lys Lys Asp Ser Ser Leu Cys Lys
        660                 665                 670

Leu Cys Met Gly Ser Gly Leu Asn Leu Cys Glu Pro Asn Asn Lys Glu
    675                 680                 685

Gly Tyr Tyr Gly Tyr Thr Gly Ala Phe Arg Cys Leu Val Glu Lys Gly
690                 695                 700

Asp Val Ala Phe Val Lys His Gln Thr Val Pro Gln Asn Thr Gly Gly
705                 710                 715                 720

Lys Asn Pro Asp Pro Trp Ala Lys Asn Leu Asn Glu Lys Asp Tyr Glu
            725                 730                 735

Leu Leu Cys Leu Asp Gly Thr Arg Lys Pro Val Glu Glu Tyr Ala Asn
        740                 745                 750

Cys His Leu Ala Arg Ala Pro Asn His Ala Val Val Thr Arg Lys Asp
    755                 760                 765

Lys Glu Ala Cys Val His Lys Ile Leu Arg Gln Gln His Leu Phe
770                 775                 780

Gly Ser Asn Val Thr Asp Cys Ser Gly Asn Phe Cys Leu Phe Arg Ser
785                 790                 795                 800

Glu Thr Lys Asp Leu Leu Phe Arg Asp Asp Thr Val Cys Leu Ala Lys
            805                 810                 815

Leu His Asp Arg Asn Thr Tyr Glu Lys Tyr Leu Gly Glu Glu Tyr Val
        820                 825                 830

Lys Ala Val Gly Asn Leu Arg Lys Cys Ser Thr Ser Leu Leu Glu
    835                 840                 845

Ala Cys Thr Phe Arg Arg Pro
850                 855

<210> SEQ ID NO 5
<211> LENGTH: 855
<212> TYPE: PRT
<213> ORGANISM: Homo sapiens

<400> SEQUENCE: 5

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

```
Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
            85                  90                  95

Pro Glu Leu Gly Pro Thr Leu Asp Thr Leu Gln Leu Asp Val Ala Asp
        100                 105                 110

Phe Ala Thr Cys Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
        130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro Gly Ser
                165                 170                 175

Val Pro Asp Lys Thr Val Arg Trp Cys Ala Val Ser Glu His Glu Ala
            180                 185                 190

Thr Lys Cys Gln Ser Phe Arg Asp His Met Lys Ser Val Ile Pro Ser
        195                 200                 205

Asp Gly Pro Ser Val Ala Cys Val Lys Lys Ala Ser Tyr Leu Asp Cys
        210                 215                 220

Ile Arg Ala Ile Ala Ala Asn Glu Ala Asp Ala Val Thr Leu Asp Ala
225                 230                 235                 240

Gly Leu Val Tyr Asp Ala Tyr Leu Ala Pro Asn Asn Leu Lys Pro Val
                245                 250                 255

Val Ala Glu Phe Tyr Gly Ser Lys Glu Asp Pro Gln Thr Phe Tyr Tyr
            260                 265                 270

Ala Val Ala Val Val Lys Lys Asp Ser Gly Phe Gln Met Asn Gln Leu
        275                 280                 285

Arg Gly Lys Lys Ser Cys His Thr Gly Leu Gly Arg Ser Ala Gly Trp
        290                 295                 300

Asn Ile Pro Ile Gly Leu Leu Tyr Cys Asp Leu Pro Glu Pro Arg Lys
305                 310                 315                 320

Pro Leu Glu Lys Ala Val Ala Asn Phe Phe Ser Gly Ser Cys Ala Pro
            325                 330                 335

Cys Ala Asp Gly Thr Asp Phe Pro Gln Leu Cys Gln Leu Cys Pro Gly
        340                 345                 350

Cys Gly Cys Ser Thr Leu Asn Gln Tyr Phe Gly Tyr Ser Gly Ala Phe
        355                 360                 365

Lys Cys Leu Lys Asp Gly Ala Gly Asp Val Ala Phe Val Lys His Ser
        370                 375                 380

Thr Ile Phe Glu Asn Leu Ala Asn Lys Ala Asp Arg Asp Gln Tyr Glu
385                 390                 395                 400

Leu Leu Cys Leu Asp Asn Thr Arg Lys Pro Val Asp Glu Tyr Lys Asp
            405                 410                 415

Cys His Leu Ala Gln Val Pro Ser His Thr Val Val Ala Arg Ser Met
        420                 425                 430

Gly Gly Lys Glu Asp Leu Ile Trp Glu Leu Leu Asn Gln Ala Gln Glu
        435                 440                 445

His Phe Gly Lys Asp Lys Ser Lys Glu Phe Gln Leu Phe Ser Ser Pro
        450                 455                 460

His Gly Lys Asp Leu Leu Phe Lys Asp Ser Ala His Gly Phe Leu Lys
465                 470                 475                 480
```

Val Pro Pro Arg Met Asp Ala Lys Met Tyr Leu Gly Tyr Glu Tyr Val
            485                 490                 495

Thr Ala Ile Arg Asn Leu Arg Glu Gly Thr Cys Pro Glu Ala Pro Thr
        500                 505                 510

Asp Glu Cys Lys Pro Val Lys Trp Cys Ala Leu Ser His His Glu Arg
            515                 520                 525

Leu Lys Cys Asp Glu Trp Ser Val Asn Ser Val Gly Lys Ile Glu Cys
        530                 535                 540

Val Ser Ala Glu Thr Thr Glu Asp Cys Ile Ala Lys Ile Met Asn Gly
545                 550                 555                 560

Glu Ala Asp Ala Met Ser Leu Asp Gly Gly Phe Val Tyr Ile Ala Gly
                565                 570                 575

Lys Cys Gly Leu Val Pro Val Leu Ala Glu Asn Tyr Asn Lys Ser Asp
            580                 585                 590

Asn Cys Glu Asp Thr Pro Glu Ala Gly Tyr Phe Ala Val Ala Val Val
        595                 600                 605

Lys Lys Ser Ala Ser Asp Leu Thr Trp Asp Asn Leu Lys Gly Lys Lys
610                 615                 620

Ser Cys His Thr Ala Val Gly Arg Thr Ala Gly Trp Asn Ile Pro Met
625                 630                 635                 640

Gly Leu Leu Tyr Asn Lys Ile Asn His Cys Arg Phe Asp Glu Phe Phe
                645                 650                 655

Ser Glu Gly Cys Ala Pro Gly Ser Lys Lys Asp Ser Ser Leu Cys Lys
            660                 665                 670

Leu Cys Met Gly Ser Gly Leu Asn Leu Cys Glu Pro Asn Asn Lys Glu
        675                 680                 685

Gly Tyr Tyr Gly Tyr Thr Gly Ala Phe Arg Cys Leu Val Glu Lys Gly
690                 695                 700

Asp Val Ala Phe Val Lys His Gln Thr Val Pro Gln Asn Thr Gly Gly
705                 710                 715                 720

Lys Asn Pro Asp Pro Trp Ala Lys Asn Leu Asn Glu Lys Asp Tyr Glu
                725                 730                 735

Leu Leu Cys Leu Asp Gly Thr Arg Lys Pro Val Glu Glu Tyr Ala Asn
            740                 745                 750

Cys His Leu Ala Arg Ala Pro Asn His Ala Val Val Thr Arg Lys Asp
        755                 760                 765

Lys Glu Ala Cys Val His Lys Ile Leu Arg Gln Gln Gln His Leu Phe
770                 775                 780

Gly Ser Asn Val Thr Asp Cys Ser Gly Asn Phe Cys Leu Phe Arg Ser
785                 790                 795                 800

Glu Thr Lys Asp Leu Leu Phe Arg Asp Asp Thr Val Cys Leu Ala Lys
                805                 810                 815

Leu His Asp Arg Asn Thr Tyr Glu Lys Tyr Leu Gly Glu Glu Tyr Val
            820                 825                 830

Lys Ala Val Gly Asn Leu Arg Lys Cys Ser Thr Ser Ser Leu Leu Glu
        835                 840                 845

Ala Cys Thr Phe Arg Arg Pro
    850                 855

<210> SEQ ID NO 6
<211> LENGTH: 2097
<212> TYPE: DNA
<213> ORGANISM: Artificial
<220> FEATURE:
<223> OTHER INFORMATION: pcDNA3.1(+)/preTf vector

<400> SEQUENCE: 6

```
atgaggctcg ccgtgggagc cctgctggtc tgcgccgtcc tggggctgtg tctggctgtc    60
cctgataaaa ctgtgagatg gtgtgcagtg tcggagcatg aggccactaa gtgccagagt   120
ttccgcgacc atatgaaaag cgtcattcca tccgatggtc ccagtgttgc ttgtgtgaag   180
aaagcctcct accttgattg catcagggcc attgcggcaa acgaagcgga tgctgtgaca   240
ctggatgcag gtttggtgta tgatgcttac ctggctccca taacctgaa gcctgtggtg    300
gcagagttct atgggtcaaa gaggatcca cagactttct attatgctgt tgctgtggtg    360
aagaaggata gtggcttcca gatgaaccag cttcgaggca agaagtcctg ccacacgggt   420
ctaggcaggt ccgctgggtg aacatcccc ataggcttac tttactgtga cttacctgag    480
ccacgtaaac tcttgagaa agcagtggcc aatttcttct cgggcagctg tgccccttgt   540
gcggatggga cggacttccc ccagctgtgt caactgtgtc cagggtgtgg ctgctccacc   600
cttaaccaat acttcggcta tcaggagcc ttcaagtgtc tgaaggatgg tgctggggat    660
gtggcctttg tcaagcactc gactatattt gagaacttgg caaacaaggc tgacagggac   720
cagtatgagc tgcttttgcct ggacaacacc cggaagccgg tagatgaata caaggactgc   780
cacttggccc aggtcccttc tcataccgtc gtggcccgaa gtatgggcgg caaggaggac   840
ttgatctggg agcttctcaa ccaggcccag gaacattttg gcaaagacaa atcaaaagaa   900
ttccaactat tcagctctcc tcatgggaag gacctgctgt ttaaggactc tgcccacggg   960
ttttttaaaag tccccccag gatggatgcc aagatgtacc tgggctatga gtatgtcact   1020
gccatccgga atctacggga aggcacatgc ccagaagccc aacagatga atgcaagcct   1080
gtgaagtggt gtgcgctgag ccaccacgag aggctcaagt gtgatgagtg gagtgttaac   1140
agtgtaggga aaatagagtg tgtatcagca gagaccaccg aagactgcat cgccaagatc   1200
atgaatggag aagctgatgc catgagcttg gatggagggt ttgtctacat agcgggcaag   1260
tgtggtctgg tgcctgtctt ggcagaaaac tacaataaga gcgataattg tgaggataca   1320
ccagaggcag ggtatttgc tgtagcagtg gtgaagaaat cagcttctga cctcacctgg   1380
gacaatctga aaggcaagaa gtcctgccat acggcagttg gcagaaccgc tggctggaac   1440
atccccatgg gcctgctcta caataagatc aaccactgca gatttgatga atttttcagt   1500
gaaggttgtg cccctgggtc taagaaagac tccagtctct gtaagctgtg tatgggctca   1560
ggcctaaacc tgtgtgaacc caacaacaaa gagggatact acggctacac aggcgctttc   1620
aggtgtctgt tgagaaggg agatgtggcc tttgtgaaac accagactgt cccacagaac   1680
actgggggaa aaaaccctga tccatgggct aagaatctga tgaaaaaga ctatgagttg   1740
ctgtgccttg atggtaccag gaaacctgtg gaggagtatg cgaactgcca cctggccaga   1800
gccccgaatc acgctgtggt cacacggaaa gataaggaag cttgcgtcca caagatatta   1860
cgtcaacagc agcaccactt tggaagcaac gtaactgact gctcgggcaa cttttgttg   1920
ttccggtcgg aaaccaagga ccttctgttc agagatgaca cagtatgttt ggccaaactt   1980
catgacagaa acacatatga aaatactta ggagaagaat atgtcaaggc tgttggtaac   2040
ctgagaaaat gctccacctc atcactcctg gaagcctgca ctttccgtag accttaa    2097
```

<210> SEQ ID NO 7
<211> LENGTH: 2097
<212> TYPE: DNA
<213> ORGANISM: Artificial
<220> FEATURE:

<223> OTHER INFORMATION: pcDNA3.1(+)/preTf(B) vector

<400> SEQUENCE: 7

```
atgaggctcg ccgtgggagc cctgctggtc tgcgccgtcc tggggctgtg tctggctgtc      60
cctgataaaa ctgtgagatg gtgtgcagtg tcggagcatg aggccactaa gtgccagagt     120
ttccgcgacc atatgaaaag cgtcattcca tccgatggtc ccagtgttgc ttgtgtgaag     180
aaagcctcct accttgattg catcagggcc attgcggcaa acgaagcgga tgctgtgaca     240
ctggatgcag gtttggtgta tgatgcttac ctggctccca taacctgaa gcctgtggtg      300
gcagagttct atgggtcaaa agaggaccca cagactttct attatgctgt tgctgtggtg     360
aagaaggata gtggcttcca gatgaaccag cttcgaggca gaagtcctg ccacacgggt      420
ctaggcaggt ccgctgggtg gaacatcccc ataggcttac tttactgtga cttacctgag     480
ccacgtaaac ctcttgagaa agcagtggcc aatttcttct cgggcagctg tgccccttgt    540
gcggatggga cggacttccc ccagctgtgt caactgtgtc cagggtgtgg ctgctccacc    600
cttaaccaat acttcggcta ctcaggagcc ttcaagtgtc tgaaggatgg tgctggggat    660
gtggcctttg tcaagcactc gactatattt gagaacttgg caaacaaggc tgacagggac    720
cagtatgagc tgctttgcct ggacaacacc cggaagccgg tagatgaata caaggactgc    780
cacttggccc aggtccct tc tcataccgtc gtggcccgaa gtatgggcgg caaggaggac    840
ttgatctggg agcttctcaa ccaggcccag gaacattttg gcaaagacaa atcaaaagaa    900
ttccaactat tcagctctcc tcatgggaag gacctgctgt ttaaggactc tgcccacggg    960
tttttaaaag tccccccccag gatggatgcc aagatgtacc tgggctatga gtatgtcact   1020
gccatccgga atctacggga aggcacatgc ccagaagccc aacagatga atgcaagcct    1080
gtgaagtggt gtgcgctgag ccaccacgag aggctcaagt gtgatgagtg gagtgttaac   1140
agtgtaggga aaatagagtg tgtatcagca gagaccaccg aagactgcat cgccaagatc   1200
atgaatggaa agctgatgc catgagcttg gatggagggt ttgtctacat agcgggcaag    1260
tgtggtctgg tgcctgtctt ggcagaaaac tacaataaga gcgataattg tgaggataca   1320
ccagaggcag ggtattttgc cgtagcagtg gtgaagaaat cagcttctga cctcacctgg   1380
gacaatctga aaggcaagaa gtcctgccat acggcagttg gcagaaccgc tggctggaac   1440
atccccatgg cctgctcta caataagatc aaccactgca gatttgatga atttttcagt   1500
gaaggttgtg cccctgggtc taagaaagac tccagtctct gtaagctgtg tatgggctca   1560
ggcctaaacc tgtgtgaacc caacaacaaa gagggatact acggctacac aggcgctttc   1620
aggtgtctgg ttgagaaggg agatgtggcc tttgtgaaac accagactgt cccacagaac   1680
actgggggaa aaaccctga tccatgggct aagaatctga tgaaaaaga ctatgagttg     1740
ctgtgccttg atggtaccag gaaacctgtg gaggagtatg cgaactgcca cctggccaga   1800
gccccgaatc acgctgtggt cacacggaaa gataaggaag cttgcgtcca caagatatta   1860
cgtcaacagc agcaccctatt tggaagcaac gtaactgact gctcgggcaa cttttgtttg   1920
ttccggtcgg aaaccaagga ccttctgttc agagatgaca cagtatgttt ggccaaactt   1980
catgacagaa acacatatga aaaatactta ggagaagaat atgtcaaggc tgttggtaac   2040
ctgagaaaat gctccaccctc atcactcctg gaagcctgca cttccgtag accttaa      2097
```

<210> SEQ ID NO 8
<211> LENGTH: 2040
<212> TYPE: DNA
<213> ORGANISM: Artificial

<220> FEATURE:
<223> OTHER INFORMATION: pcDNA3.1(+)/Tf(B) vector

<400> SEQUENCE: 8

```
gtccctgata aaactgtgag atggtgtgca gtgtcggagc atgaggccac taagtgccag      60
agtttccgcg accatatgaa aagcgtcatt ccatccgatg gtcccagtgt tgcttgtgtg     120
aagaaagcct cctaccttga ttgcatcagg gccattgcgg caaacgaagc ggatgctgtg     180
acactggatc aggtttggt gtatgatgct tacctggctc ccaataacct gaagcctgtg     240
gtggcagagt tctatgggtc aaaagaggac ccacagactt tctattatgc tgttgctgtg     300
gtgaagaagg atagtggctt ccagatgaac cagcttcgag gcaagaagtc ctgccacacg     360
ggtctaggca ggtccgctgg gtggaacatc cccataggct tactttactg tgacttacct     420
gagccacgta aacctcttga gaaagcagtg gccaatttct tctcgggcag ctgtgccact     480
tgtgcggatg ggacggactt ccccagctg tgtcaactgt gtccagggtg tggctgctcc     540
acccttaacc aatacttcgg ctactcagga gccttcaagt gtctgaagga tggtgctggg     600
gatgtggcct ttgtcaagca ctcgactata tttgagaact tggcaaacaa ggctgacagg     660
gaccagtatg agctgctttg cctggacaac acccggaagc cggtagatga atacaaggac     720
tgccacttgg cccaggtccc ttctcatacc gtcgtggccc gaagtatggg cggcaaggag     780
gacttgatct gggagcttct caaccaggcc caggaacatt ttggcaaaga caaatcaaaa     840
gaattccaac tattcagctc tcctcatggg aaggacctgc tgtttaagga ctctgcccac     900
gggttttaa aagtcccccc caggatggat gccaagatgt acctgggcta tgagtatgtc     960
actgccatcc ggaatctacg ggaaggcaca tgcccagaag ccccaacaga tgaatgcaag    1020
cctgtgaagt ggtgtgcgct gagccaccac gagaggctca agtgtgatga gtggagtgtt    1080
aacagtgtag ggaaaataga gtgtgtatca gcagagacca ccgaagactg catcgccaag    1140
atcatgaatg gagaagctga tgccatgagc ttggatggag ggtttgtcta catagcgggc    1200
aagtgtggtc tggtgcctgt cttggcagaa aactacaata gagcgataa ttgtgaggat    1260
acaccagagg cagggtattt tgctgtagca gtggtgaaga atcagcttc tgacctcacc    1320
tgggacaatc tgaaaggcaa gaagtcctgc catacgcgca ttggcagaac cgctggctgg    1380
aacatcccca tgggcctgct ctacaataag atcaaccact gcagatttga tgaatttttc    1440
agtgaaggtt gtgcccctgg gtctaagaaa gactccagtc tctgtaagct gtgtatgggc    1500
tcaggcctaa acctgtgtga acccaacaac aaagagggat actacggcta cacaggcgct    1560
ttcaggtgtc tggttgagaa gggagatgtg gcctttgtga acaccagac tgtcccacag    1620
aacactgggg gaaaaaaccc tgatccatgg gctaagaatc tgaatgaaaa agactatgag    1680
ttgctgtgcc ttgatggtac caggaaacct gtggaggagt atgcgaactg ccacctggcc    1740
agagccccga tcacgctgt ggtcacacgg aaagataagg aagcttgcgt ccacaagata    1800
ttacgtcaac agcagcacct atttggaagc aacgtaactg actgctcggg caacttttgt    1860
ttgttccggt cggaaaccaa ggaccttctg ttcagagatg acacagtatg tttggccaaa    1920
cttcatgaca gaaacacata tgaaaaatac ttaggagaag aatatgtcaa ggctgttggt    1980
aacctgagaa aatgctccac ctcatcactc ctggaagcct gcactttccg tagaccttaa    2040
```

<210> SEQ ID NO 9
<211> LENGTH: 36
<212> TYPE: DNA
<213> ORGANISM: Artificial
<220> FEATURE:

<223> OTHER INFORMATION: PCR primer

<400> SEQUENCE: 9
catgctagct ccaccatgag gctcgccgtg ggagcc                                    36

<210> SEQ ID NO 10
<211> LENGTH: 31
<212> TYPE: DNA
<213> ORGANISM: Artificial
<220> FEATURE:
<223> OTHER INFORMATION: PCR primer2

<400> SEQUENCE: 10
agactcgagt taaggtctac ggaaagtgca g                                        31

<210> SEQ ID NO 11
<211> LENGTH: 35
<212> TYPE: DNA
<213> ORGANISM: Artificial
<220> FEATURE:
<223> OTHER INFORMATION: PCR primer3

<400> SEQUENCE: 11
ctatgggtca aaagaggacc cacagacttt ctatt                                    35

<210> SEQ ID NO 12
<211> LENGTH: 35
<212> TYPE: DNA
<213> ORGANISM: Artificial
<220> FEATURE:
<223> OTHER INFORMATION: PCR primer4

<400> SEQUENCE: 12
aatagaaagt ctgtgggtcc tcttttgacc catag                                    35

<210> SEQ ID NO 13
<211> LENGTH: 16
<212> TYPE: PRT
<213> ORGANISM: Homo sapiens

<400> SEQUENCE: 13

Met Arg Leu Ala Val Gly Ala Leu Leu Val Cys Ala Val Leu Gly Leu
1               5                   10                  15

<210> SEQ ID NO 14
<211> LENGTH: 32
<212> TYPE: DNA
<213> ORGANISM: Artificial
<220> FEATURE:
<223> OTHER INFORMATION: PCR primer5

<400> SEQUENCE: 14
ctcggatccg tccctgataa aactgtgaga tg                                       32

<210> SEQ ID NO 15
<211> LENGTH: 36
<212> TYPE: DNA
<213> ORGANISM: Artificial
<220> FEATURE:
<223> OTHER INFORMATION: 6PCR primer

<400> SEQUENCE: 15
catgctagct ccaccatggc tggacctgcc acccag                                   36

<210> SEQ ID NO 16

```
<211> LENGTH: 27
<212> TYPE: DNA
<213> ORGANISM: Artificial
<220> FEATURE:
<223> OTHER INFORMATION: PCR primer7

<400> SEQUENCE: 16
catggatccg ggctgggcaa ggtggcg                                     27

<210> SEQ ID NO 17
<211> LENGTH: 20
<212> TYPE: DNA
<213> ORGANISM: Artificial
<220> FEATURE:
<223> OTHER INFORMATION: PCR primer8

<400> SEQUENCE: 17
taatacgact cactataggg                                             20

<210> SEQ ID NO 18
<211> LENGTH: 35
<212> TYPE: DNA
<213> ORGANISM: Artificial
<220> FEATURE:
<223> OTHER INFORMATION: PCR primer9

<400> SEQUENCE: 18
aatagaaagt ctgtgggtcc tcctttgacc catag                            35

<210> SEQ ID NO 19
<211> LENGTH: 32
<212> TYPE: DNA
<213> ORGANISM: Artificial
<220> FEATURE:
<223> OTHER INFORMATION: PCR primer10

<400> SEQUENCE: 19
gccgactttg ccacctgcat ctggcagcag at                               32

<210> SEQ ID NO 20
<211> LENGTH: 32
<212> TYPE: DNA
<213> ORGANISM: Artificial
<220> FEATURE:
<223> OTHER INFORMATION: PCR primer11

<400> SEQUENCE: 20
atctgctgcc agatgcaggt ggcaaagtcg gc                               32

<210> SEQ ID NO 21
<211> LENGTH: 2658
<212> TYPE: DNA
<213> ORGANISM: Artificial
<220> FEATURE:
<223> OTHER INFORMATION: pcDNA3.1(+)/G-CSF(T116C)-Tf vector

<400> SEQUENCE: 21
atggctggac ctgccaccca gagccccatg aagctgatgg ccctgcagct gctgctgtgg    60
cacagtgcac tctggacagt gcaggaagcc acccccctgg ccctgccagc tccctgccc   120 cagagcttcc tgctcaagtg cttagagcaa gtgaggaaga tccagggcga tggcgcagcg   180
ctccaggaga agctgtgtgc cacctacaag ctgtgccacc cgaggagct ggtgctgctc   240 ggacactctc tggcatccc ctgggctccc ctgagcagct gccccagcca ggccctgcag   300
ctggcaggct gcttgagcca actccatagc ggccttttcc tctaccaggg gctcctgcag   360
```

```
gccctggaag ggatctcccc cgagttgggt cccaccttgg acacactgca gctggacgtc    420
gccgactttg ccacctgcat ctggcagcag atgaagaac tgggaatggc ccctgccctg    480
cagcccaccc agggtgccat gccggccttc gcctctgctt tccagcgccg ggcaggaggg    540
gtcctggttg cctcccatct gcagagcttc tggaggtgt cgtaccgcgt tctacgccac    600
cttgcccagc ccggatccgt ccctgataaa actgtgagat ggtgtgcagt gtcggagcat    660
gaggccacta agtgccagag tttccgcgac catatgaaaa gcgtcattcc atccgatggt    720
cccagtgttg cttgtgtgaa gaaagcctcc taccttgatt gcatcagggc cattgcggca    780
aacgaagcgg atgctgtgac actggatgca ggtttggtgt atgatgctta cctggctccc    840
aataacctga agcctgtggt ggcagagttc tatgggtcaa agaggaccc acagactttc    900 tattatgctg ttgctgtggt gaagaaggat agtggcttcc agatgaacca gcttcgaggc    960
aagaagtcct gccacacggg tctaggcagg tccgctgggt ggaacatccc cataggctta   1020
ctttactgtg acttacctga gccacgtaaa cctcttgaga aagcagtggc caatttcttc   1080
tcgggcagct gtgccccttg tgcggatggg acggacttcc cccagctgtg tcaactgtgt   1140
ccagggtgtg gctgctccac ccttaaccaa tacttcggct actcaggagc cttcaagtgt   1200
ctgaaggatg gtgctgggga tgtggccttt gtcaagcact cgactatatt tgagaacttg   1260
gcaaacaagg ctgacaggga ccagtatgag ctgctttgcc tggacaacac ccggaagccg   1320
gtagatgaat acaaggactg ccacttggcc caggtccctt ctcataccgt cgtggcccga   1380
agtatgggcg gcaaggagga cttgatctgg gagcttctca accaggccca ggaacatttt   1440
ggcaaagaca aatcaaaaga attccaacta ttcagctctc ctcatgggaa ggacctgctg   1500
tttaaggact ctgcccacgg gttttttaaa gtcccccca ggatggatgc caagatgtac   1560
ctgggctatg agtatgtcac tgccatccgg aatctacggg aaggcacatg cccagaagcc   1620
ccaacagatg aatgcaagcc tgtgaagtgg tgtgcgctga ccaccacga gaggctcaag   1680 tgtgatgagt ggagtgttaa cagtgtaggg aaaatagagt gtgtatcagc agagaccacc   1740
gaagactgca tcgccaagat catgaatgga gaagctgatg ccatgagctt ggatggaggg   1800
tttgtctaca tagcgggcaa gtgtggtctg gtgcctgtct tggcagaaaa ctacaataag   1860
agcgataatt gtgaggatac accagaggca gggtattttg ctgtagcagt ggtgaagaaa   1920
tcagcttctg acctcacctg gacaatctg aaaggcaaga agtcctgcca tacggcagtt   1980
ggcagaaccg ctggctggaa catccccatg ggcctgctct acaataagat caaccactgc   2040
agatttgatg aattttttcag tgaaggttgt gcccctgggt ctaagaaaga ctccagtctc   2100
tgtaagctgt gtatgggctc aggcctaaac ctgtgtgaac ccaacaacaa agagggatac   2160
tacggctaca caggcgcttt caggtgtctg gttgagaagg gagatgtggc ctttgtgaaa   2220
caccagactg tcccacagaa cactgggga aaaaaccctg atccatgggc taagaatctg   2280
aatgaaaaag actatgagtt gctgtgcctt gatggtacca ggaaacctgt ggaggagtat   2340
gcgaactgcc acctggccag agccccgaat cacgctgtgg tcacacggaa agataaggaa   2400
gcttgcgtcc acaagatatt acgtcaacag cagcacctat ttggaagcaa cgtaactgac   2460
tgctcgggca cttttgttt gttccggtcg gaaaccaagg accttctgtt cagagatgac   2520
acagtatgtt tggccaaact tcatgacaga aacacatatg aaaaatactt aggagaagaa   2580
tatgtcaagg ctgttggtaa cctgagaaaa tgctccacct catcactcct ggaagcctgc   2640
actttccgta gacccttaa                                                 2658
```

PHARMACEUTICAL COMPOSITIONS CONTAINING, AS ACTIVE INGREDIENT, GRANULOCYTE-COLONY STIMULATING FACTOR MUTANT PROTEIN OR TRANSFERRIN FUSION PROTEIN THEREOF

CROSS-REFERENCE TO RELATED APPLICATIONS

This application claims priority to PCT Application No. PCT/KR2014/011269 filed Nov. 21, 2014, entitled "Pharmaceutical Composition Containing, As Active Ingredient, Granulocytecolony Stimulating Factor Mutant Protein or Transferrin Fusion Protein Thereof," which claims the benefit of and priority to Korean Patent Application No. 10-2014-0093260, filed on Jul. 23, 2014 and Korean Patent Application No. 10-2014-0137414, filed on Oct. 13, 2014. All the aforementioned applications are incorporated by reference herein in their entirety.

BACKGROUND OF THE INVENTION

1. Field of the Invention

The present invention relates to a fusion protein in which transferrin is peptide-bonded to a terminal of a granulocyte-colony stimulating factor (G-CSF) protein or a G-CSF mutant protein.

2. Description of the Related Art

Granulocyte-colony stimulating factor (G-CSF) is a glycoprotein that stimulates survival, proliferation, differentiation, and functions of neutrophil and granulocyte progenitor cells and mature neutrophils.

The natural G-CSF which is now being used clinically is called 'Filgrastim', and is a recombinant protein composed of 175 amino acids originated from human amino acid sequence. This recombinant protein is expressed in E. coli and is not glycosylated unlike the natural type.

G-CSF is used as an anticancer adjuvant for the prevention of infectious complications caused by neutropenia accompanied by cancer treatment by stimulating neutrophil granulopoiesis. G-CSF demonstrates a beneficial clinical effect on cancer patients because it can reduce side effects of febrile neutropenia caused by chemo-therapy or radio-therapy for cancer treatment and thereby can reduce death rate by chemo-therapy for cancer treatment. G-CSF increases the number of hematopoietic progenitor cells and accordingly reduces the side effects above.

It is also known that G-CSF stimulates bone marrow stem cells to move ischemic heart and accelerates differentiation of the stem cells into vascular cells and cardiomyocytes by stimulating myocardial regeneration.

The recombinant human G-CSF (rhG-CSF) displays pharmacological effects only for a short time. Therefore, it has to be administered at least once a day to treat ischemic disease or to treat leukopenia caused by anticancer chemotherapy or radio-therapy. If a substance having a long in vivo half-life is administered, the administration times necessary for relieving leukopenia would be reduced and as a result it could bring the effect of preventing infectious complications.

When Polyethylene glycol (PEG), the chemical polymer that is not degraded in vivo, is fused to the N-terminal of G-CSF, a substance called 'Pegfilgrastim' is produced. This substance is clinically used for the treatment of leukopenia. This substance has an increased in vivo half-life and displays a clinical effect while leukopenia continues even with the administration performed once or twice a week. However, in that case, a protein is fused with a chemical polymer by chemical reaction, and thus the problems of unsatisfactory fusion efficiency and complicated purification method can be caused.

Cysteine, the $17^{th}$ amino acid of G-CSF is exposed on the protein surface as nonsulfated binding state. In neutral pH, the exposed cysteine is combined with adjacent G-CSF cysteine via sulfide bond and as a result it loses its activity. A G-CSF mutant wherein the $17^{th}$ cysteine is substituted with serine displays increased stability in neutral pH, according to the previous reports.

Transferrin is the third most abundant protein in blood plasma, which serves to transport iron ions present in the blood to various tissues. Transferrin has a relatively long half-life of 8 days, which is shorter than that of albumin or immunoglobulin G. It enters the cell through the transferrin receptor on the surface of the cell and once it supplies iron ions, it is released to the outside of the cell in a state of binding with the receptor. Using these characteristics, transferrin has been used as a fusion partner to increase circulating half-life by combining the proteins with short half-lives of the prior art.

In this invention, threonine, the $116^{th}$ amino acid of human G-CSF, was substituted with cysteine to induce sulfide bonding with the $17^{th}$ cysteine of the original amino acid sequence of G-CSF. Sulfide bonding makes the protein structure more stable so that the protein can be resistant against proteases, that is the protein now has a protease resistance. The attempt to have a protease resistance through the construction of such a mutant protein is new and the effect thereof has not been reported yet.

There has been no reports of using the mutant protein of G-CSF wherein the $116^{th}$ amino acid is replaced with cysteine for the fusion with transferrin to increase blood half-life of G-CSF.

The present inventors succeeded in making a fusion protein of transferrin and the mutant protein of human G-CSF wherein the $116^{th}$ amino acid was replaced with cysteine and further confirmed that the fusion protein had significantly increased specific activity and blood stability, compared with the unfused original human G-CSF, leading to the completion of this invention.

SUMMARY OF THE INVENTION

It is an object of the present invention to provide a fusion protein in which transferrin is peptide-bonded to a terminal of a granulocyte-colony stimulating factor (G-CSF) protein or a G-CSF mutant protein in which the $116^{th}$ threonine is substituted with cysteine in the amino acid sequence of the G-CSF.

To achieve the above object, the present invention provides a fusion protein in which transferrin is peptide-bonded to a terminal of a granulocyte-colony stimulating factor (G-CSF) protein or a G-CSF mutant protein in which the $116^{th}$ threonine is substituted with cysteine in the amino acid sequence of the G-CSF, a G-CSF mutant protein in which the $116^{th}$ threonine is replaced with cysteine, and a use of the same.

The present invention also provides a pharmaceutical composition and an anticancer adjuvant for preventing or treating ischemic diseases or neutropenia comprising the fusion protein in which transferrin is peptide-bonded to a terminal of a granulocyte-colony stimulating factor (G-CSF) protein or a G-CSF mutant protein in which the $116^{th}$ threonine is substituted with cysteine in the amino acid sequence of the G-CSF or the G-CSF mutant protein in which the $116^{th}$ threonine is replaced with cysteine as an active ingredient.

The present invention also provides an expression vector containing the gene encoding a fusion protein in which transferrin is peptide-bonded to a terminal of a granulocyte-colony stimulating factor (G-CSF) protein or a G-CSF mutant protein in which the $116^{th}$ threonine is substituted with cysteine in the amino acid sequence of the G-CSF or a G-CSF mutant protein in which the $116^{th}$ threonine is replaced with cysteine and a transformant prepared by inserting the expression vector above in a host cell.

The present invention also provides a method for preparing the expression vector containing the gene encoding a fusion protein in which transferrin is peptide-bonded to a terminal of a granulocyte-colony stimulating factor (G-CSF) protein or a G-CSF mutant protein in which the $116^{th}$ threonine is substituted with cysteine in the amino acid sequence of the G-CSF or a G-CSF mutant protein in which the $116^{th}$ threonine is replaced with cysteine, and the transformant prepared by inserting the expression vector above in a host cell.

The present invention also provides a method for preventing or treating neutropenia or ischemic disease containing the step of administering the fusion protein in which transferrin is peptide-bonded to a terminal of a granulocyte-colony stimulating factor (G-CSF) protein or a G-CSF mutant protein in which the $116^{th}$ threonine is substituted with cysteine in the amino acid sequence of the G-CSF, the G-CSF mutant protein in which the $116^{th}$ threonine is replaced with cysteine, the expression vector, or the transformant above to a subject having neutropenia or ischemic disease.

The present invention also provides a method for reducing neutrophils containing the step of administering the fusion protein in which transferrin is peptide-bonded to a terminal of a granulocyte-colony stimulating factor (G-CSF) protein or a G-CSF mutant protein in which the $116^{th}$ threonine is substituted with cysteine in the amino acid sequence of the G-CSF, the G-CSF mutant protein in which the $116^{th}$ threonine is replaced with cysteine, the expression vector, or the transformant above to a subject.

In addition, the present invention provides a use of the fusion protein in which transferrin is peptide-bonded to a terminal of a granulocyte-colony stimulating factor (G-CSF) protein or a G-CSF mutant protein in which the $116^{th}$ threonine is substituted with cysteine in the amino acid sequence of the G-CSF, the G-CSF mutant protein in which the $116^{th}$ threonine is replaced with cysteine, the expression vector, or the transformant above.

Advantageous Effect

The granulocyte-colony stimulating factor (G-CSF) mutant protein of the present invention or the transferrin fusion protein thereof displays a significantly increased specific activity and blood stability, compared with the conventional human G-CSF, and has a higher purification efficiency than the conventional PEGylated G-CSF characterized by the extended half-life, so that it can be advantageously used for preventing or treating ischemic diseases or neutropenia.

BRIEF DESCRIPTION OF THE DRAWINGS

The application of the preferred embodiments of the present invention is best understood with reference to the accompanying drawings, wherein:

FIG. 1 is a diagram illustrating the cleavage map of pcDNA3.1(+)/preTf vector.

FIG. 2 is a diagram illustrating the cleavage map of pcDNA3.1(+)/preTf(B) vector.

FIG. 3 is a diagram illustrating the cleavage map of pcDNA3.1(+)/Tf(B) vector.

FIG. 4 is a diagram illustrating the cleavage map of pcDNA3.1(+)/G-CSF(T116C)-Tf vector.

FIG. 5 is a diagram illustrating the expression of G-CSF (T116C)-Tf in the cell line Expi293F transfected with G-CSF(T116C)-Tf plasmid.

FIG. 6 is a diagram illustrating the G-CSF(T116C)-Tf protein separated by DEAE Affi-gel blue chromatography.

FIG. 7 is a diagram illustrating the preparation, concentration, and separation of $Fe^{3+}$ fused G-CSF(T116C)-Tf in the form of holo (holoenzyme).

FIG. 8 is a diagram illustrating the binding force of G-CSF(T116C)-Tf in the form of holo to the transferrin receptor.

FIG. 9 is a diagram illustrating the cell proliferation activity of HL-60 cells treated with G-CSF, G-CSF-Tf, and G-CSF(T116C)-Tf.

FIG. 10 is a diagram illustrating the comparison of protease resistance between G-CSF and G-CSF(T116C).

FIG. 11 is a diagram illustrating the comparison of in vivo plasma half-life between G-CSF-Tf and G-CSF(T116C)-Tf.

FIG. 12 is a diagram illustrating the comparison of physiological activity between G-CSF and G-CSF(T116C)-Tf in the rat having neutropenia.

DESCRIPTION OF THE PREFERRED EMBODIMENTS

Hereinafter, the present invention is described in detail.

The present invention provides a fusion protein in which transferrin is peptide-bonded to a terminal of a granulocyte-colony stimulating factor (G-CSF) protein or a G-CSF mutant protein in which the $116^{th}$ threonine is substituted with cysteine in the amino acid sequence of the G-CSF, a G-CSF mutant protein in which the $116^{th}$ threonine is replaced with cysteine, and a use of the same.

The G-CSF or transferrin used in this invention can be originated from animals, plants, or microorganisms. It is more preferably human originated G-CSF or transferrin herein, but it can be also a heterologous protein having the equal activity to human originated G-CSF or transferrin.

The protein above can additionally be modified such as phosphorylation, acetylation, methylation, glycosylation, etc., or it can be fused with another protein. As long as the function of the protein is not lost, such mutant protein can be considered as the same as the protein before any modification.

Another amino acid that can replace the $116^{th}$ threonine is a hydrophobic amino acid, which is more precisely cysteine that is possibly linked to the $17^{th}$ cysteine of G-CSF sequence via disulfide bond, but not always limited thereto.

The terminal where transferrin is bound can be either the amino terminal (5'-end, N-terminal) or the carboxy terminal (3'-end, C-terminal).

The said granulocyte-colony stimulating factor (G-CSF) protein is the protein represented by SEQ. ID. NO: 1 but this sequence may have addition, deletion, or substitution of one or more amino acids in its sequence as long as the gene encoding the G-CSF is located at the same position on the chromosome and the activity is not changed.

The granulocyte-colony stimulating factor (G-CSF) protein above preferably has at least 80% homology, more preferably at least 90% homology, and most preferably at least 95%, 96%, 97%, 98%, 99%, or 99.5% homology to the amino acid sequence represented by SEQ. ID. NO: 1, but not always limited thereto.

The said transferrin is the protein represented by SEQ. ID. NO: 2 but this sequence may have addition, deletion, or substitution of one or more amino acids in its sequence as long as the gene encoding the transferrin is located at the same position on the chromosome and the activity is not changed.

The transferrin protein above preferably has at least 80% homology, more preferably at least 90% homology, and most preferably at least 95%, 96%, 97%, 98%, 99%, or 99.5% homology to the amino acid sequence represented by SEQ. ID. NO: 2, but not always limited thereto.

The said granulocyte-colony stimulating factor (G-CSF) mutant protein is the protein represented by SEQ. ID. NO: 3 but this sequence may have addition, deletion, or substitution of one or more amino acids in its sequence as long as the gene encoding the transferrin is located at the same position on the chromosome and the activity is not changed.

The granulocyte-colony stimulating factor (G-CSF) mutant protein above preferably has at least 80% homology, more preferably at least 90% homology, and most preferably at least 95%, 96%, 97%, 98%, 99%, or 99.5% homology to the amino acid sequence represented by SEQ. ID. NO: 3, but not always limited thereto.

The fusion protein in which transferrin is peptide-bonded to a terminal of G-CSF preferably has at least 80% homology, more preferably at least 90% homology, and most preferably at least 95%, 96%, 97%, 98%, 99%, or 99.5% homology to the amino acid sequence represented by SEQ. ID. NO: 4, but not always limited thereto.

The fusion protein in which transferrin is peptide-bonded to a terminal of a G-CSF mutant protein in which the $116^{th}$ threonine is substituted with cysteine in the amino acid sequence of the G-CSF preferably has at least 80% homology, more preferably at least 90% homology, and most preferably at least 95%, 96%, 97%, 98%, 99%, or 99.5% homology to the amino acid sequence represented by SEQ. ID. NO: 5, but not always limited thereto.

The said G-CSF, the G-CSF mutant protein in which the $116^{th}$ threonine is substituted with cysteine in the amino acid sequence of the G-CSF, or the transferrin may have the substitution of nucleotide sequence for gene manipulation. For example the nucleotide sequence of a restriction enzyme recognition site in the gene can be substituted with another nucleotide sequence encoding another amino acid which is equal to the original amino acid but not causing any changes in the protein activity, or a part of the gene terminal can be deleted, substituted or added with a restriction enzyme recognition site. For example, thymine of the BamHI restriction enzyme recognition site of the protein gene, GGATCC, can be substituted with cytosine, but not always limited thereto.

The said restriction enzyme is exemplified by EcoRI, BamHI, HindIII, kpnI, NotI, PstI, SmaI, XhoI, FokI, Alw26I, BbvI, BsrI, EarI, HphI, MboI, SfaNI, Tth111I, NaeI, NheI, NgoMIV, NheI, Eco57I, BcgI, BpI, Bsp24I, BaeI, CjeI, EcoPI, HintIII, and StyLTI, etc. However, any restriction enzyme that is used in the art can be used according to the gene, expression vector or genetic manipulation environment without limitation.

The present invention also provides a pharmaceutical composition for preventing or treating neutropenia and ischemic disease comprising the fusion protein in which transferrin is peptide-bonded to a terminal of a G-CSF mutant protein in which the $116^{th}$ threonine is substituted with cysteine in the amino acid sequence of the G-CSF or the G-CSF mutant protein in which the $116^{th}$ threonine is substituted with cysteine in the amino acid sequence of the G-CSF as an active ingredient, an anticancer adjuvant comprising the same, an expression vector comprising a gene encoding the said protein, and a transformant prepared by inserting the said expression vector in a host cell.

The term 'neutropenia' in this invention indicates the abnormal reduction of neutrophils. When the number of blood neutrophils is less than 1500/µl, it is classified as light neutropenia and when the number of blood neutrophils is less than 1000/µl, it is classified as moderate neutropenia. When the number of blood neutrophils is less than 500/µl, it is classified as severe neutropenia. In a large sense, leukopenia (neucopenia) is also included in neutropenia.

The 'ischemic disease' of the present invention is caused by cell damage caused when the blood supply to the tissue is interrupted by hemorrhage, embolism, and infarction, etc, which is exemplified by trauma, graft rejection, stroke, cerebral infraction, ischemic renal disease, ischemic lung disease, infection mediated ischemic disease, ischemic limb disease, ischemic cardiomyopathy, myocardial infarction, and heart failure, etc.

The said another amino acid that can replace the $116^{th}$ threonine can be a hydrophobic amino acid, which is precisely cysteine that is suitable for disulfide bond, but not always limited thereto.

The said granulocyte-colony stimulating factor (G-CSF) protein is the protein represented by SEQ. ID. NO: 1 but this sequence may have addition, deletion, or substitution of one or more amino acids in its sequence as long as the gene encoding the G-CSF is located at the same position on the chromosome and the activity is not changed.

The granulocyte-colony stimulating factor (G-CSF) protein above preferably has at least 80% homology, more preferably at least 90% homology, and most preferably at least 95%, 96%, 97%, 98%, 99%, or 99.5% homology to the amino acid sequence represented by SEQ. ID. NO: 1, but not always limited thereto.

The said transferrin is the protein represented by SEQ. ID. NO: 2 but this sequence may have addition, deletion, or substitution of one or more amino acids in its sequence as long as the gene encoding the transferrin is located at the same position on the chromosome and the activity is not changed.

The transferrin protein above preferably has at least 80% homology, more preferably at least 90% homology, and most preferably at least 95%, 96%, 97%, 98%, 99%, or 99.5% homology to the amino acid sequence represented by SEQ. ID. NO: 2, but not always limited thereto.

The said granulocyte-colony stimulating factor (G-CSF) mutant protein is the protein represented by SEQ. ID. NO: 3 but this sequence may have addition, deletion, or substitution of one or more amino acids in its sequence as long as the gene encoding the transferrin is located at the same position on the chromosome and the activity is not changed.

The granulocyte-colony stimulating factor (G-CSF) mutant protein above preferably has at least 80% homology, more preferably at least 90% homology, and most preferably at least 95%, 96%, 97%, 98%, 99%, or 99.5% homology to the amino acid sequence represented by SEQ. ID. NO: 3, but not always limited thereto.

The fusion protein in which transferrin is peptide-bonded to a terminal of G-CSF preferably has at least 80% homology, more preferably at least 90% homology, and most preferably at least 95%, 96%, 97%, 98%, 99%, or 99.5% homology to the amino acid sequence represented by SEQ. ID. NO: 4, but not always limited thereto.

The fusion protein in which transferrin is peptide-bonded to a terminal of a G-CSF mutant protein in which the 116$^{th}$ threonine is substituted with another amino acid in the amino acid sequence of the G-CSF but this sequence may have addition, deletion, or substitution of one or more amino acids in its sequence as long as the gene encoding the G-CSF or transferrin is located at the same position on the chromosome and the activity is not changed.

The fusion protein in which transferrin is peptide-bonded to a terminal of a G-CSF mutant protein in which the 116$^{th}$ threonine is substituted with another amino acid in the amino acid sequence of the G-CSF preferably has at least 80% homology, more preferably at least 90% homology, and most preferably at least 95%, 96%, 97%, 98%, 99%, or 99.5% homology to the amino acid sequence represented by SEQ. ID. NO: 5, but not always limited thereto.

The said G-CSF, the G-CSF mutant protein in which 116$^{th}$ threonine is substituted with another amino acid in the amino acid sequence of the G-CSF, or the transferrin may have the substitution of nucleotide sequence for gene manipulation. For example the nucleotide sequence of a restriction enzyme recognition site in the gene can be substituted with another nucleotide sequence encoding another amino acid which is equal to the original amino acid but not causing any changes in the protein activity, or a part of the gene terminal can be deleted, substituted or added with a restriction enzyme recognition site. For example, thymine of the BamHI restriction enzyme recognition site of the protein gene, GGATCC, can be substituted with cytosine, but not always limited thereto.

The said restriction enzyme is exemplified by EcoRI, BamHI, kpnI, NotI, PstI, SmaI, XhoI, FokI, Alw26I, BbvI, BsrI, EarI, HphI, MboI, SfaNI, Tth111I, NaeI, NheI, NgoMIV, NheI, Eco57I, BcgI, BpI, Bsp24I, BaeI, CjeI, EcoPI, HintIII, and StyLTI, etc. However, any restriction enzyme that is used in the art can be used according to the gene, expression vector or genetic manipulation environment without limitation.

The 'expression vector' of the invention is a tool to introduce the nucleic acid sequence encoding a target protein into a host cell, which includes plasmid, cosmid, BAC, and virus nucleic acid, etc. The said vector generally includes a selection marker such as an antibiotic resistant gene that can confirm the successful introduction of a target gene into a host cell. The vector can further include promoter, operator, initiation codon, stop codon, polyadenylated sequence, enhancer, Kozak sequence, and Shine-Dalgarno sequence, etc, for the expression of a target gene. If the vector is a replicable expression vector, it can contain a replication origin.

The host cell herein can be selected from the group consisting of *E. coli*, yeast, fungi, plant cells, and animal cells, but not always limited thereto and any host cell that is used for the production of a recombinant protein in this field can be accepted.

The pharmaceutical composition of the present invention can be prepared for oral or parenteral administration by mixing with generally used diluents or excipients such as fillers, extenders, binders, wetting agents, disintegrating agents and surfactant. Solid formulations for oral administration are tablets, pills, powders, granules and capsules. These solid formulations are prepared by mixing with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The pharmaceutical composition of the present invention can be administered orally or parenterally, and the parenteral administration includes skin external application, intrarectal injection, intravenous injection, intramuscular injection, hypodermic injection, intrathoracic injection, or intracerebroventricular injection.

The effective dosage of the pharmaceutical composition can be determined according to weight, age, gender, health condition, diet, administration frequency, administration method, excretion and severity of disease, but these cannot limit the present invention by any means. An individual dosage preferably contains the amount of active compound that is suitable for being administered in a single dose.

The single dose herein for the protein is 1~100 mg, preferably 3~50 mg, and more preferably 6~30 mg, which can be administered once a day or several times a day and can be administered dividedly to different parts.

The pharmaceutical composition of the present invention can be administered alone or treated together with surgical operation, hormone therapy, chemo-therapy and biological regulators.

The present invention also provides a method for preparing a fusion protein in which transferrin is peptide-bonded to a terminal of a granulocyte-colony stimulating factor (G-CSF) protein or a G-CSF mutant protein in which the 116$^{th}$ threonine is substituted with cysteine in the amino acid sequence of the G-CSF, a G-CSF mutant protein in which the 116$^{th}$ threonine is replaced with cysteine, an expression vector containing the gene encoding a fusion protein in which transferrin is peptide-bonded to a terminal of a granulocyte-colony stimulating factor (G-CSF) protein or a G-CSF mutant protein in which the 116$^{th}$ threonine is substituted with cysteine in the amino acid sequence of the G-CSF or a G-CSF mutant protein in which the 116$^{th}$ threonine is replaced with cysteine, and a transformant prepared by inserting the expression vector above in a host cell.

The protein herein can be obtained by chemical synthesis or produced from natural cells, or purified from transfected host cells via recombinant DNA technology. The obtained protein may have an additional modification such as phosphorylation, acetylation, methylation, and glycosylation, or can be as fused with another protein, but such modification is allowed as long as the function of the protein is not changed.

The method for preparing the protein using recombinant DNA technology is composed of the following steps:

inserting a target gene for expression in an expression vector;

introducing the expression vector to a host cell; and obtaining the protein produced by culturing the host cell.

However, the production of the protein is not limited to the above and any method known to those in the art can be used.

The step of obtaining the protein can be performed by using a purification technique well-known to those in the art, which is exemplified by protein precipitation, centrifugation, ultrasonic disruption, ultrafiltration, dialysis, gel filtration, adsorption chromatography, ion exchange chromatography, and affinity chromatography.

In a preferred embodiment of the present invention, a restriction enzyme recognition site was eliminated from the transferrin gene, and instead a restriction enzyme site was inserted in the 5'-end and also a restriction enzyme site and a stop codon were inserted in 3'-end, resulting in the construction of a plasmid. In the plasmid was inserted the gene having the deletion of a restriction enzyme recognition site from G-CSF sequence, resulting in the construction of a plasmid wherein transferrin gene was fused with G-CSF gene.

In a preferred embodiment of the present invention, a G-CSF mutant was prepared by replacing the $116^{th}$ amino acid of G-CSF sequence with cysteine. A restriction enzyme recognition site was eliminated from the gene and instead a restriction enzyme site and Kozak sequence were inserted in the 5'-end and a restriction enzyme site was also inserted in 3'-end, resulting in the construction of a plasmid. Then, transferrin gene was fused with the plasmid above to construct a plasmid wherein transferrin gene was fused with G-CSF mutant gene.

The present invention also provides a method for preventing or treating neutropenia or ischemic disease containing the step of administering the fusion protein in which transferrin is peptide-bonded to a terminal of a granulocyte-colony stimulating factor (G-CSF) protein or a G-CSF mutant protein in which the $116^{th}$ threonine is substituted with cysteine in the amino acid sequence of the G-CSF, the G-CSF mutant protein in which the $116^{th}$ threonine is replaced with cysteine, the expression vector harboring the gene encoding the said protein, or the transformant prepared by inserting the said expression vector to a host cell to a subject having neutropenia or ischemic disease.

The granulocyte-colony stimulating factor (G-CSF) mutant protein of the present invention or the transferrin fusion protein thereof displays a significantly increased specific activity and blood stability, compared with the conventional human G-CSF, and has a higher purification efficiency than the conventional PEGylated G-CSF characterized by the extended half-life, so that it can be advantageously used for preventing or treating ischemic diseases or neutropenia.

The present invention also provides a method for reducing neutrophils containing the step of administering the fusion protein in which transferrin is peptide-bonded to a terminal of a granulocyte-colony stimulating factor (G-CSF) protein or a G-CSF mutant protein in which the $116^{th}$ threonine is substituted with cysteine in the amino acid sequence of the G-CSF, the G-CSF mutant protein in which the $116^{th}$ threonine is replaced with cysteine, the expression vector, or the transformant above to a subject.

The granulocyte-colony stimulating factor (G-CSF) mutant protein of the present invention or the transferrin fusion protein thereof displays a significantly increased specific activity and blood stability, compared with the conventional human G-CSF, and has a higher purification efficiency than the conventional PEGylated G-CSF characterized by the extended half-life, so that it can be advantageously used for reducing neutrophils In addition, the present invention provides a use of the fusion protein in which transferrin is peptide-bonded to a terminal of a granulocyte-colony stimulating factor (G-CSF) protein or a G-CSF mutant protein in which the $116^{th}$ threonine is substituted with cysteine in the amino acid sequence of the G-CSF, the G-CSF mutant protein in which the $116^{th}$ threonine is replaced with cysteine, the expression vector, or the transformant above.

The granulocyte-colony stimulating factor (G-CSF) mutant protein of the present invention or the transferrin fusion protein thereof displays a significantly increased specific activity and blood stability, compared with the conventional human G-CSF, and has a higher purification efficiency than the conventional PEGylated G-CSF characterized by the extended half-life, so that it can be advantageously used as an anticancer adjuvant, and used for preventing or treating ischemic diseases or neutropenia.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Plasmid Construction

<1-1> Construction of Transferrin Expression Plasmid

Total mRNA was obtained from the human hepatocellular carcinoma cell line HepG2. HepG2 cells were sub-cultured in DMEM (HyClone) supplemented with 10% fetal bovine serum (WELGENE) and 1% penicillin-streptomycin (Gibco) in a 37° C., 5% $CO_2$ incubator. Two days later, the HepG2 cell culture medium was discarded and the cells were washed with phosphate buffer (HyClone). The cell pellet was obtained, and the medium was eliminated by centrifugation. Then, the cell pellet was stored at −70° C. The frozen cells stored at −70° C. were thawed and total mRNA was extracted therefrom by using RnaUs ToTal Tissue Premium RNA Preps (LeGene) with the standard conditions presented in the manual. cDNA was synthesized from the obtained total mRNA by using oligo (dT) with Premium Express $1^{st}$ Strand cDNA synthesis system (LeGene).

PCR was performed by using the synthesized cDNA as a template with DNA polymerase (Phusion). The primers used in the reaction were custom-made in Cosmogenetech Co., Ltd. Particularly, NheI restriction enzyme site and Kozak sequence were inserted in the 5'-end of the transferrin gene and Xho I restriction enzyme site and stop codon (TAA) were inserted in the 3'-end of the gene. 10 pmol of a sense primer (5'-CATGCTAGCTCCACCATGAGGCTCGC-CGTGGGAGCC-3', SEQ. ID. NO: 9) and 10 pmol of an antisense primer (5'-AGACTCGAGTTAAGGTCTACG-GAAAGTGCAG-3', SEQ. ID. NO: 10) were used. The primers, DNA polymerase, and cDNA were mixed with buffer, to which distilled water was added to make the total volume 50 μl. PCR was performed as follows; predenaturation at 98° C. for 30 seconds, denaturation at 98° C. for 10 seconds, annealing at 53° C. for 30 seconds, polymerization at 72° C. for 1 minute, 30 cycles from denaturation to polymerization, and final extension at 72° C. for 10 minutes. The amplified transferrin gene was transferred onto 1% agarose-gel for electrophoresis to confirm the size. The target area of the agarose-gel was cut off and DNA was purified by using MEGAquick-spin™ Total Fragment DNA purification kit (iNtRoN).

The purified transferrin gene and pcDNA3.1(+) plasmid (Invitrogen) were digested with the restriction enzymes NheI (Enzynomics) and XhoI (Enzynomics). 10 unit of the restriction enzyme and buffer 2 (10 mM Tris-HCL pH 7.9, 50 mM NaCl, 10 mM MgCl$_2$, 1 mM DTT, 100 µg/ml BSA) were added thereto, followed by reaction at 37° C. for 2~3 hours. Upon completion of the reaction, the size of the gene was confirmed by 1% agarose-gel electrophoresis. The target area of the agarose-gel was cut off and DNA was purified by using MEGAquick-spin™ Total Fragment DNA purification kit (iNtRoN).

The purified transferrin gene and pcDNA3.1(+) vector were reacted with T4 DNA ligase (Takara) at 16° C. for 16 hours. Upon completion of the reaction, the vector was inserted in *E. coli* DH10B, which was distributed on Agar plate containing ampicillin, followed by culture at 37° C. for 16 hours. Then, *E. coli* colony was selected.

To investigate whether or not the transferrin gene was successfully inserted in pcDNA3.1(+) plasmid, PCR was performed by using DNA polymerase. The selected *E. coli* colony was diluted in water, which was used as a template, followed by PCR with the sense primer (5'-CATGCTAGCTCCACCATGAGGCTCGCCGTGGGAGCC-3', SEQ. ID. NO: 9) and the antisense primer (5'-AGACTCGAGTTAAGGTCTACGGAAAGTGCAG-3', SEQ. ID. NO: 10) used for the transferrin gene amplification above. PCR was performed as follows; predenaturation at 98° C. for 30 seconds, denaturation at 98° C. for 10 seconds, annealing at 53° C. for 30 seconds, polymerization at 72° C. for 1 minute, 30 cycles from denaturation to polymerization, and final extension at 72° C. for 10 minutes. Upon completion of the PCR, electrophoresis on 1% agarose-gel was performed to confirm the gene.

The confirmed *E. coli* colony was inoculated in a LB liquid medium (1% trypton, 0.5% yeast extract, 1% NaCl), followed by culture at 37° C. for 16 hours in a shaking incubator. The cultured *E. coli* was centrifuged to separate the supernatant and the cell pellet. Plasmid DNA was purified from the cell pellet using Exprep™ Plasmid SV,mini (GeneAll). Sequencing of the purified plasmid was performed by Cosmogenetech Co., Ltd. The prepared transferrin expression plasmid was named in this invention 'pcDNA3.1(+)/preTf (SEQ. ID. NO: 6)' (FIG. 1).

To use the BamHI restriction enzyme site for the construction of a plasmid, the BamHI site on the transferrin gene was mutated by site-direct mutagenesis to eliminate the BamHI restriction enzyme site. To eliminate the BamHI restriction enzyme site from the transferrin gene, thymine (T) was replaced with cytosine (C) but the amino acid sequence was maintained by aspartic acid. To replace the BamHI restriction enzyme site, GGATCC, with the sequence GGACCC, the sense primer (5'-CTATGGGTCAAAAGAGGACCCACAGACTTTCTATT-3', SEQ. ID. NO: 11) and the antisense primer (5'-AATAGAAAGTCTGTGGGTCCTCTTTTGACCCATAG-3', SEQ. ID. NO: 12) custom-made in Cosmogenetech Co., Ltd. were used. Site-direct mutagenesis was performed using the prepared pcDNA3.1(+)/preTf plasmid as a template by using Muta-direct Site Directed Mutagenesis kit (iNtRON) according to the manufacturer's protocol. Upon completion of the reaction, the gene was confirmed by electrophoresis on 1% agarose-gel. The confirmed *E. coli* colony was inoculated in a LB liquid medium containing ampicillin, followed by culture at 37° C. for 16 hours in a shaking incubator. The cultured *E. coli* was centrifuged to separate the supernatant and the cell pellet. Plasmid DNA was purified from the cell pellet using a plasmid extraction kit (GeneAll). The substitution of nucleic acid of the BamHI restriction enzyme site on the transferrin gene was confirmed by sequencing. The prepared plasmid was named in this invention 'pcDNA3.1(+)/preTf(B) (SEQ. ID. NO: 7)' (FIG. 2).

Transferrin is a secretary protein that contains a signal peptide to help the transportation of a protein synthesized on N-terminal to cell membrane. Transferrin is composed of the amino acid sequence 'MRLAVGALLVCAVLGLCLA (SEQ. ID. NO: 13)'. To insert a human leukocytopoiesis stimulating factor gene into the 5'-end of the transferrin gene, the signal peptide of the transferrin was eliminated and the restriction enzyme BamHI was placed in the 5'-end instead, resulting in the construction of a plasmid. In the 3' end were inserted XhoI and Stop codon (TAA). PCR was performed by using pcDNA3.1(+)/preTf(B) as a template in the presence of DNA polymerase. Xho I restriction enzyme site and stop codon (TAA) were inserted in the 3'-end of the gene. PCR was performed by using pcDNA3.1(+)/preTf(B) as a template with DNA polymerase. The primers used in the reaction were custom-made in Cosmogenetech Co., Ltd. 10 pmol of a sense primer (5'-CTCGGATCCGTCCCTGATAAAACTGTGAGATG-3', SEQ. ID. NO: 14) and 10 pmol of an antisense primer (5'-AGACTCGAGTTAAGGTCTACGGAAAGTGCAG-3', SEQ. ID. NO: 10) were used. The primers, DNA polymerase, and template were mixed with buffer, to which distilled water was added to make the total volume 50 µl. PCR was performed as follows; predenaturation at 98° C. for 30 seconds, denaturation at 98° C. for 10 seconds, annealing at 53° C. for 30 seconds, polymerization at 72° C. for 1 minute, 30 cycles from denaturation to polymerization, and final extension at 72° C. for 10 minutes. The amplified transferrin gene was transferred onto 1% agarose-gel for electrophoresis to confirm the size. The target area of the agarose-gel was cut off and DNA was purified by using MEGAquick-spin™ Total Fragment DNA purification kit (iNtRoN). The purified transferrin gene and pcDNA3.1(+) plasmid were digested with the restriction enzymes BamHI (Enzynomics) and XhoI (Enzynomics). 10 unit of the restriction enzyme and buffer 2 (10 mM Tris-HCL pH 7.9, 50 mM NaCl, 10 mM MgCl$_2$, 1 mM DTT, 100 µg/ml BSA) were added thereto, followed by reaction at 37° C. for 2~3 hours. Upon completion of the reaction, the size of the gene was confirmed by 1% agarose-gel electrophoresis. The target area of the agarose-gel was cut off and DNA was purified by using MEGAquick-spin™ Total Fragment DNA purification kit (iNtRoN). The purified transferrin gene and pcDNA3.1(+) vector proceeded to electrophoresis on 1% agarose-gel again, followed by DNA quantification. The transferrin gene and pcDNA3.1(+) vector were reacted with T4 DNA ligase (Takara) at 16° C. for 16 hours. Upon completion of the reaction, the vector was inserted in *E. coli* DH10B, which was distributed on Agar plate containing ampicillin, followed by culture at 37° C. for 16 hours. Then, *E. coli* colony was selected. To investigate whether or not the transferrin gene was successfully inserted in pcDNA3.1(+) plasmid, PCR was performed. The selected *E. coli* colony was diluted in water, which was used as a template, followed by PCR with the sense primer (5'-CTCGGATCCGTCCCTGATAAAACTGTGAGATG-3', SEQ. ID. NO: 14) and the antisense primer (5'-AGACTCGAGTTAAGGTCTACGGAAAGTGCAG-3', SEQ. ID. NO: 10)

used for the transferrin gene amplification above. PCR was performed as follows; predenaturation at 98° C. for 30 seconds, denaturation at 98° C. for 10 seconds, annealing at 53° C. for 30 seconds, polymerization at 72° C. for 1 minute, 30 cycles from denaturation to polymerization, and final extension at 72° C. for 10 minutes. Upon completion of the PCR, electrophoresis on 1% agarose-gel was performed to confirm the gene. The confirmed *E. coli* colony was inoculated in a LB liquid medium (1% trypton, 0.5% yeast extract, 1% NaCl), followed by culture at 37° C. for 16 hours in a shaking incubator. The cultured *E. coli* was centrifuged to separate the supernatant and the cell pellet. Plasmid DNA was purified from the cell pellet using Exprep™ Plasmid SV,mini (GeneAll). The insertion of the transferrin gene without signal peptide was confirmed by sequencing. The prepared plasmid was named in this invention 'pcDNA3.1 (+)/Tf(B) (SEQ. ID. NO: 8)' (FIG. 3).

<1-2> Construction of G-CSF-Tf Expression Plasmid

To eliminate the BamHI restriction enzyme site from pcDNA6/G-CSF, pcDNA6/G-CSF plasmid was treated with 20 units of BamHI (Enzynomics), followed by reaction at 37° C. for 3 hours. The reacted plasmid (45 ng) was amplified by PCR with 10 pmol of a sense primer (5'-CATGCTAGCTCCACCA TGGCTGGACCTGCCAC-CCAG-3', SEQ. ID. NO: 15) and an antisense primer (5'-CATGGATCCGGGCTGGGCAAGGTGGCG-3', SEQ. ID. NO: 16). As a result, a G-CSF gene fragment having Nhe I restriction enzyme site and Kozak sequence in the 5'-end and BamHI restriction enzyme site in the 3'-end was prepared. 1 μg of the prepared G-CSF gene fragment and 365 ng of pcDNA3.1(+)/Tf(B) plasmid were reacted with 10 units of NheI restriction enzyme and 20 units of BamHI restriction enzyme respectively for at 37° C. for 4 hours. Electrophoresis was performed on DNA agarose-gel (0.5× TAE, 1% agarose). To construct pcDNA3.1(+)/G-CSF-Tf, the purified pcDNA3.1(+)/Tf(B) plasmid and the G-CSF gene fragment were mixed at the molar ratio of 1:3, which was reacted with 350 U of T4 DNA ligase at 25° C. for 1 hour. Then, *E. coli* DH5α was transfected with the reaction product. Colonies showing resistance against ampicillin were selected. Colony PCR was performed to confirm the construction of pcDNA3.1(+)/G-CSF-Tf plasmid. Particularly, the colonies selected from the transfected *E. coli* DH5α were amplified by colony PCR with 10 pmol of the sense primer (5'-TAATACGACTCACTATAGGG-3', SEQ. ID. NO: 17) and the antisense primer (5'-AATA-GAAAGTCTGTGGGTCCTCCTTTGACCCATAG-3', SEQ. ID. NO: 18). The size of the amplified product was confirmed on agarose-gel (0.5×TAE, 1% agarose). The confirmed colony was inoculated in a LB liquid medium (trypton 50 mg, yeast extract 25 mg, and sodium chloride 50 mg per 5 ml) containing ampicillin (100 μg/ml), followed by culture for 15 hours. pcDNA3.1(+)/G-CSF-Tf was extracted by using a plasmid extraction kit. The successful construction of pcDNA3.1(+)/G-CSF-Tf was confirmed by sequencing.

<1-3> Construction of G-CSF(T116C) and G-CSF(T116C)-Tf Expression Plasmid 10 pmol of the sense primer (5'-GCCGACTTTGCCAC-CTGCATCTGGCAGCAGAT-3', SEQ. ID. NO: 19) and the antisense primer (5'-ATCTGCTGCCAGATGCAGGTG-GCAAAGTCGGC-3', SEQ. ID. NO: 20) were mixed with pET21a(+)/G-CSF, followed by PCR. Site-directed mutagenesis was performed by the same manner as described in Example <1-1> to construct G-CSF(T116C). The resultant plasmid was named in this invention 'pET21a(+)/G-CSF (T116C)'.

The size of pET21a(+)/G-CSF(T116C) was confirmed by DNA agarose-gel (0.5×TAE, 1% agarose) electrophoresis. The target area of the agarose-gel was cut off and DNA was purified by using a gel purification kit (Cosmogenetech). *E. coli* DH10B was transfected with the purified pET21a(+)/G-CSF(T116C). Colonies showing resistance against ampicillin were selected. The selected colony was inoculated in a LB liquid medium (trypton 50 mg, yeast extract 25 mg, and sodium chloride 50 mg per 5 ml) containing ampicillin (100 μg/ml), followed by culture for 15 hours. pET21a(+)/G-CSF(T116C) was extracted by using a plasmid extraction kit. Sequencing was performed and as a result, the successful substitution of the nucleotide sequence was confirmed.

First, the sense primer (5'-GCCGACTTTGCCACCTG-CATCTGGCAGCAGAT-3', SEQ. ID. NO: 19) and the antisense primer (5'-ATCTGCTGCCAGATGCAGGTG-GCAAAGTCGGC-3', SEQ. ID. NO: 20) were dissolved respectively to the concentration of 10 pmol/μl. 10 pmol of each primer was taken for PCR with 100 ng of the G-CSF gene (100 ng) inserted in pcDNA6. Site-directed mutagenesis was performed by the same manner as described in Example <1-1> to obtain G-CSF(T116C) gene. The obtained plasmid was named in this invention 'pcDNA6/G-CSF(T116C).

The size of pcDNA6/G-CSF(T116C) was confirmed by DNA agarose-gel (0.5×TAE, 1% agarose) electrophoresis. The target area of the agarose-gel was cut off and DNA was purified by using a gel purification kit (Cosmogenetech). *E. coli* DH10B was transfected with the purified pcDNA6/G-CSF(T116C)). Colonies showing resistance against ampicillin were selected. The selected colony was inoculated in a LB liquid medium (trypton 50 mg, yeast extract 25 mg, and sodium chloride 50 mg per 5 ml) containing ampicillin (100 μg/ml), followed by culture for 15 hours. pcDNA6/G-CSF (T116C) was extracted by using a plasmid extraction kit. Sequencing was performed and as a result, the successful substitution of the nucleotide sequence was confirmed. To eliminate the BamHI restriction enzyme site from pcDNA6/G-CSF(T116C), 1 μg of pcDNA6/G-CSF(T116C) plasmid was treated with 20 units of BamHI (Enzynomics), followed by reaction at 37° C. for 3 hours. The reacted plasmid (45 ng) was amplified by PCR with 10 pmol of a sense primer (5'-CATGCTAGCTCCACCA TGGCTGGACCTGCCAC-CCAG-3', SEQ. ID. NO: 15) and an antisense primer (5'-CATGGATCCGGGCTGGGCAAGGTGGCG-3', SEQ. ID. NO: 16). As a result, a G-CSF(T116C) DNA fragment having Nhe I restriction enzyme site and Kozak sequence in the 5'-end and BamHI restriction enzyme site in the 3'-end was prepared. 1 μg of the prepared G-CSF(T116C) DNA fragment and 365 ng of pcDNA3.1(+)/Tf(B) plasmid were reacted with 10 units of NheI restriction enzyme and 20 units of BamHI restriction enzyme respectively for at 37° C. for 4 hours. Electrophoresis was performed on DNA agarose-gel (0.5×TAE, 1% agarose), followed by purification by using a gel extraction kit. To construct pcDNA3.1(+)/G-CSF (T116C)-Tf, the purified pcDNA3.1(+)/Tf(B) plasmid and the G-CSF(T116C) DNA fragment were mixed at the molar ratio of 1:3, which was reacted with 350 U of T4 DNA ligase at 25° C. for 1 hour. Then, *E. coli* DH5α was transfected with the reaction product. Colonies showing resistance against ampicillin were selected. Colony PCR was performed to confirm the construction of pcDNA3.1(+)/G-CSF (T116C)-Tf plasmid. Particularly, the colonies selected from the transfected *E. coli* DH5α were amplified by colony PCR with 10 pmol of the sense primer (5'-TAATACGACTCAC-TATAGGG-3', SEQ. ID. NO: 17) and the antisense primer (5'-AATAGAAAGTCTGTGGGTCCTCCTTTGAC- CCATAG-3', SEQ. ID. NO: 18). The size of the amplified product was confirmed on agarose-gel (0.5×TAE, 1% agarose). The confirmed colony was inoculated in a LB liquid medium (trypton 50 mg, yeast extract 25 mg, and sodium chloride 50 mg per 5 ml) containing ampicillin (100 μg/ml), followed by culture for 15 hours. pcDNA3.1(+)/G-CSF (T116C)-Tf was extracted by using a plasmid extraction kit. The successful construction of pcDNA3.1(+)/G-CSF (T116C)-Tf (SEQ. ID. NO: 21) was confirmed by sequencing.

Example 2: Protein Expression Through Transient Transfection

<2-1> Expression of G-CSF(T116C)

1 μl of pET21a(+)/G-CSF(T116C) plasmid was inoculated in 20 μl of Rosetta2 (DE3), the expression strain, followed by reaction at 42° C. for 90 seconds for transfection. The transfected expression strain was smeared on LB plate containing ampicillin (50 μg/mL), followed by culture at 37° C. for 15 hours to obtain colonies. The colonies were inoculated in 100 mL of LB medium containing ampicillin (50 μg/mL) and chloramphenicol (25 μg/mL), followed by culture at 37° C. for 15 hours. 20 mL of the cultured strain was inoculated in 1 L of LB medium containing ampicillin (50 μg/mL) and chloramphenicol (25 μg/mL), followed by culture with stirring at 37° C. for 4 hours until $OD_{600}$ reached 0.8. 1 mM IPTG was added thereto, followed by stirring culture at 37° C. for 4 hours. Centrifugation was performed at 6000 rpm for 15 minutes to separate the supernatant and the precipitate respectively. The expression of the protein as an inclusion body was confirmed by SDS-PAGE.

<2-2> Expression of G-CSF(T116C)-Tf

The proteins used in this invention were expressed by extracellular secretion using Expi293F™ (Gibco), the human embryonic kidney cancer cell line modified for suspension culture. Expi293F™ cells included in Expi293F™ Expression system Kit (Gibco) were first thawed, which were inoculated in a sterilized 125 mL flask (Thermo) containing 30 mL of serum-free medium for animal cell culture (Gibco), followed by shaking culture at 125 rpm in a 37° C., 5% $CO_2$ incubator.

The density of Expi293F™ cell line was maintained at 3~5×10⁶ cells/mL. Sub-culture was performed every 3~4 days. After stabilized, the cells were inoculated in serum-free medium at the density of 2×10⁶ cells/mL for transfection, followed by shaking culture for 24 hours. Just before the transfection, the cell density was adjusted to 2×10⁶ cells/mL and the cell survival rate was confirmed at least 90% before the following experiment.

22.5 μg of G-CSF-Tf and G-CSF(T116C)-Tf plasmid DNA was prepared and diluted in Opti-MEM (Gibco). 45 μL of ExpiFectamine™ 293 Reagent 45 was also diluted in Opti-MEM®, which stood at room temperature for 5 minutes. The plasmid and the ExpiFectamine™ 293 Reagent mixture were well mixed, which stood at room temperature for 20 minutes. Then, the mixture was evenly distributed to the cells. 16~18 hours after the transfection, ExpiFectamine™ 293 Transfection Enhancers 1 and 2 (Gibco) were added thereto in order to increase the protein expression, followed by additional culture for 32 hours under the same shaking culture condition above. The obtained cell culture fluid was centrifuged at 2,000×g for 10 minutes and as a result the supernatant was obtained.

To confirm the protein expression, the supernatant was mixed with 5× loading dye (Biosesang), which was boiled at 95° C. for 20 minutes. The mixture was loaded on 10% SDS-PAGE, followed by electrophoresis at 160 V for 1 hour. Upon completion of the electrophoresis, the protein on the gel was transferred onto PVDF Immobilon-P-Transfer Membrane (Millipore). The membrane was reacted in 5% skim milk at room temperature for 1 hour. After washing the membrane with washing buffer (phosphate buffer containing 0.05% Tween 20), a transferrin antibody (2,000×, Santa Cruz) was added thereto, followed by reaction at room temperature for 2 hours. After washing the membrane with washing buffer again, a horseradish peroxides-conjugated antibody (10,000×, Santa Cruz) was added thereto, followed by reaction at room temperature for 1 hour. Upon completion of the antigen-antibody reaction, the membrane was washed with washing buffer and color development was induced by using SuperSignal® West Pico Chemiluminescent Substrate (Thermo). The molecular weight of G-CSF-Tf and G-CSF(T116C)-Tf was 105.7 kDa, suggesting that the protein was normally expressed (FIG. 5).

Example 3: Protein Purification

<3-1> Purification of G-CSF(T116C)

To purify the inclusion body, the cells were dissolved in a lysis buffer (50 mM Tris-Cl (pH 8.0), 2 mM EDTA, 1 mM PMSF), followed by cell lysis using an ultrasonicator (lysis time: 5 minutes, ultrasonication: 30 seconds, stand-by: 40 seconds). Centrifugation was performed at 10.000 rpm for 30 minutes at 4° C. to eliminate the supernatant. Then, the precipitate was dissolved in a washing buffer (50 mM Tris-Cl, pH 8.0, 2 mM EDTA, 0.3% Triton) and lysed using an ultrasonicator (lysis time: 5 minutes, ultrasonication: 30 seconds, stand-by: 40 seconds). Centrifugation was performed again at 10.000 rpm for 30 minutes at 4° C. to eliminate the supernatant. The precipitate was dissolved in a washing buffer (50 mM Tris-Cl, pH8.0, 2 mM EDTA, 1 M NaCl) and lysed using an ultrasonicator (lysis time: 5 minutes, ultrasonication: 30 seconds, stand-by: 40 seconds). Centrifugation was performed again at 10.000 rpm for 30 minutes at 4° C. to eliminate the supernatant. The washed inclusion body was dissolved in a solubilization buffer (8 M Urea, 50 mM Tris-Cl, pH8.0). 10 mL of the dissolved protein sample was loaded in a dialysis tube, which was left in 2 L of a dialysis buffer (50 mM Tris-Cl pH 8.0, 0.1% Tween20) at 4° C. for 16 hours for refolding. 2 M acetic acid was loaded to the reaction sample and pH was adjusted to 4.5, followed by centrifugation at 10.000 rpm for minutes at 4° C. Desalting column (17-5087-05) connected to Hiprep 26/10 AKTA prime plus FPLC was filled with a desalting buffer (25 mM Na-Acetate pH 4.5, 5% Sucrose, 0.004% Tween20). Then, buffer exchange was performed by passing the supernatant separated by centrifugation through the column above.

<3-2> Quantification of G-CSF(T116C)

The purified G-CSF(T116C) was quantified by using silver staining. The standard quantification curve was obtained by using grasin (less than 30 ng/SDS-PAGE well), the G-CSF standard material. The unknown amount of each sample was compared to the standard quantification curve so as to quantify the protein.

<3-3> Quantification of G-CSF(T116C)-Tf 30 mL of the supernatant containing G-CSF-Tf or G-CSF (T116C)-Tf was dialyzed in 4 L of 20 mM potassium phosphate buffer (pH 7.5), followed by buffer exchange. DEAE Affi-gel Blue column was filled with the G-CSF-Tf or G-CSF(T116C)-Tf included in the potassium phosphate buffer at the flow rate of 0.5 mL/min. Then, 72 mM of potassium phosphate was spilled thereon via step gradient manner and thus the proteins absorbed on the resin were separated from other proteins included in the culture fluid (FIG. 6).

<3-4> Preparation of Iron ($Fe^{3+}$) Fused Form

The preparation of the holo form of G-CSF(T116C)-Tf was based on [Zhang et al. BMC Biotechnology 2012, 12:92]. The purified G-CSF-Tf or G-CSF(T116C)-Tf was treated with the equivalent ferric ammonium citrate, followed by reaction at 37° C. for 2 hours. The mixture was dialyzed in 2 L of phosphate buffered saline at 4° C. for 15 hours, during which buffer was exchanged. The sample was 10-fold concentrated by using a concentrator (Millipore) (FIG. 7).

<3-5> Protein Quantification

The purified protein was quantified by Western blotting using a transferrin antibody. The measured transferrin was loaded in 10% SDS-PAGE at the concentrations of 15 ng, 20 ng, 25 ng, and 30 ng per each well. Another purified protein whose concentration was not determined was loaded in another well, followed by electrophoresis. Western blotting was performed to quantify the protein samples by comparing the purified protein with the transferrin standard curve.

Example 4: Investigation of Binding Force with Transferrin Receptor

Once transferrin is bound to the transferrin receptor expressed on the cell surface, it enters the cell via endocytosis. After releasing the iron, the transferrin-receptor complex moves to the cell surface again and thereafter it is secreted in blood. Transferrin repeats the process above, that is the in vivo recycling metabolism, by which it supplies the iron and avoids being decomposed in the intracellular lysosome, resulting in the increased half-life. If a target protein having a short half-life is conjugated with transferrin, the protein experiences the in vivo recycling metabolism action of transferrin together with transferrin. As a result, the target protein also can avoid being decomposed in vivo. So, the fusion protein in which G-CSF is conjugated with transferrin needs to maintain the binding force to transferrin receptor in order to avoid in vivo degradation.

To investigate the binding force of the proteins of the invention to the extracellular surface transferrin receptor (TfR), the human hepatocellular carcinoma cell line HepG2 demonstrating high expression of TfR on the cell surface was used for the following experiment. HepG2 cells were inoculated in a 96-well plate at the density of $5 \times 10^5$ cells/well, followed by culture for 24 hours. The HepG2 cells attached on the plate were washed with phosphate buffer, to which serum-free DMEM (HyClone) supplemented with 1 mg/ml of BSA (Bovine Serum Albumin) was added. The mixture stood in a 37° C., 5% $CO_2$ incubator for 30 minutes to eliminate endogenous transferrin from the cells. The cells were washed with phosphate buffer again, and then the test sample and fluorescence-labeled human transferrin Alexa Fluor® 647 (Life Technologies) were added to the serum-free DMEM supplemented with 1 mg/ml of BSA at the concentrations of 133 nM and 5 µg/mL respectively. The mixture above was treated to the HepG2 cells prepared above, which stood in a 37° C., 5% $CO_2$ incubator for 30 minutes. The protein sample remaining in the medium was washed with cold phosphate buffer. The transferrin receptor conjugated fluorescence-transferrin was quantified by fluorimetry. For the fluorimetry, light source was given at 650 nm and fluorescence intensity at 668 nm was measured.

The transferrin receptor binding force of the holo form of G-CSF(T116C)-Tf prepared in Example <3-4> was shown in FIG. 8. As a result, as shown in FIG. 8, the transferrin receptor binding force of the G-CSF-Tf or G-CSF(T116C)-Tf fusion protein was similar to that of the natural human holo-transferrin (SIGMA). This result suggests that the G-CSF-Tf or G-CSF(T116C)-Tf fusion protein can have increased half-life through experiencing the in vivo recycling due to the conjugation with the transferrin receptor, like human transferrin.

Example 5: Biological Activity of G-CSF Mutant Protein

To measure the biological activity of the purified G-CSF-Tf mutant protein, the proliferation of HL-60 cells differentiated by 1.25% DMSO was measured.

<5-1> Preparation and Treatment of Human Bone Marrow Derived Cell Line HL-60

The human bone marrow derived cell line HL-60 used in this invention was distributed from Korean Collection for Type Culture (KCTC), Korea Research Institute of Bioscience and Biotechnology (KRIBB). The cell line was cultured in RPMI-1640 containing 10% FBS in a 37° C., 5% $CO_2$ incubator. The medium was replaced with a fresh one every 2~3 days. The cells were not anchorage-dependent. The reagents for the cell culture were purchased from HyClone.

<5-2> Cell Proliferation Activity of G-CSF Mutant Protein

The number of cells was counted and the density was adjusted to be $2 \times 10^3$ cells/mL. The cells were treated with the differentiation inducer DMSO (dimethylsulfoxide, culture grade, SIGMA) at the final concentration of 1.25% (v/v), followed by culture for days to induce the differentiation into granulocytes. Before the test sample was added, the cells were collected by centrifugation and washed with phosphate buffer (D-PBS). The cells were distributed in a 96-well plate (Corning), 100 µL per each well, at the density of $4 \times 10^4$ cells/well.

The controls PEGylated human G-CSF (GenScript) and natural G-CSF (GenScript), and the test samples G-CSF-Tf, G-CSF(T116C)-Tf, and G-CSF(T116C) were diluted in desalting buffer (5 mM Sodium Phosphate, 5% Sucrose, 0.004% Tween-20), which were added to each well containing the differentiated HL-60 cells, followed by culture in a 37° C., 5% $CO_2$ incubator for 72 hours. The final concentrations of each sample were 300, 200, 100, 30, 15, 3, 0.3, and 0.03 ng/mL.

To investigate the cell proliferation level by the administration of the test samples, 15 µL of CellTiter96™ (Promega) solution was added to each well, followed by culture for 4 hours. 100 µL of solubilization/stop solution was added to each well to terminate the reaction. $OD_{570}$ of each well was measured with ELISA reader (TECAN). The increased number of cells was counted and analyzed. The cell proliferation activity of those test samples was presented as the concentration equivalent to that of G-CSF.

The cell proliferation activity of G-CSF, PEG.G-CSF, G-CSF(T116C), G-CSF-Tf, and G-CSF(T116C)-Tf is shown in FIG. 9. As shown in FIG. 9, the cell proliferation activity of G-CSF(T116C) was lower than that of the natural G-CSF but was similar to that of the PEGylated G-CSF. In the meantime, the cell proliferation activity of the G-CSF (T116C)-Tf fusion protein in which transferrin is fused with a G-CSF(T116C) mutant protein was significantly increased, compared with that of G-CSF(T116C) and was also higher than that of the PEGylated G-CSF. Therefore, since the G-CSF(T116C)-Tf displays the higher cell proliferation activity than that of the commercial PEGylated G-CSF, it is expected to be a promising candidate as an agent for the treatment particularly using G-CSF.

Example 6: Resistance Against Blood Proteases

To measure the resistance against blood proteases of the G-CSF(T116C) mutant protein of the present invention, the protein was reacted with human serum and then the amount of G-CSF remaining in the serum for a designated time was measured.

<6-1> Reaction of G-CSF with Human Serum

It was investigated whether or not the stability of the G-CSF mutant protein of the present invention was associated closely with the resistance against blood protease. Particularly, human serum (SIGMA) was inactivated at 56° C. for 30 minutes. 2.8 µg/ml of the protein sample was added thereto at the ratio of 24:1 (v/v), followed by reaction at 37° C. The reaction hours were 0, 3, 6, 9, 12, 15, and 18 hours. Complete protease inhibitor cocktail (Roche) was treated to the sample at each designated hour, which was then stored at −70° C. upon completion of the reaction.

<6-2> Measurement of Residual G-CSF

After thawing the sample, the amount of G-CSF remaining after the reaction with human serum was quantified by sandwich ELISA (Enzyme Linked Immunosorbent Assay). Calibration curve of absorbance according to the protein concentration to the standard solution was prepared and regression analysis was performed to determine the G-CSF protein content in the test solution.

The high protein binding microtiter plate (Corning) coated with a rabbit polyclonal anti-G-CSF antibody (KOMA BIOTECH) at the concentration of approximately 2 µg/ml was prepared. 1× phosphate buffer containing 1% casein sodium salt was used as a blocking buffer. The standard solution and the test solution were mixed with a buffer (10× diluted blocking buffer). The protein sample and regents were distributed by 100 µl per each well. The plate was treated with a washing buffer (1×PBS, 0.05% Tween-20) three times (300 µl/well) to wash out the non-reacted samples. The protein sample and the detection antibody (rabbit polyclonal anti-G-CSF antibody, KOMA BIOTECH) were treated thereto stepwise at room temperature for about 2 hours, followed by reaction with streptavidin-horseradish peroxidase (Pierce) at 37° C. for 30 minutes. TMB (3,3',5, 5'-tetramethylbenzidine, Pierce) was treated thereto, which stood at room temperature for about 7~10 minutes and then color development was terminated with 2 M sulfuric acid. Then, $OD_{450}$ was measured with a microplate reader (TECAN).

The absorbance was converted into concentration based on the calibration curve of protein concentration-absorbance to the standard solution. The standard curve was made using Excel program. The difference between the mean value of the absorbance corresponding to each G-CSF standard solution and the value of absorbance of the well treated with the buffer alone was calculated. For the determination of the test solution concentration, only when the absorbance value of each sample was in the range of the standard solution calibration curve, it was taken as valid. The absolute value (|R|) criterion calculated by using the correlation coefficient ($R^2$) as root ($\sqrt{}$) was set to at least 0.98. The amount of the remaining G-CSF protein (% G-CSF) was expressed by considering the concentration of G-CSF (pg/ml) at reaction time point of 0 h as 100%.

The amount (%) of remaining G-CSF and G-CSF(T116C) by time period is shown in FIG. 10. The percentage of remaining G-CSF(T116C) was approximately 30% higher than that of natural G-CSF since 15 hours after the reaction started. It was confirmed that the disulfide bond between Cys116 and Cys17 was helpful for the increase of resistance of the protein against blood protease.

Example 7: Measurement of In Vivo Half-Life of G-CSF Mutant Proteins

To investigate the in vivo half-life of the G-CSF mutant protein and the transferrin fusion protein of the invention, the proteins were administered to mice and then the level of G-CSF in the rat serum was measured. The mentioned 'in vivo half-life' indicates the 'half-life of protein in serum'. That is, the time point when the G-CSF protein level was down to 50% by the initial concentration during its circulation in serum was expressed numerically. Pharmacokinetic calculation was performed using PKsolver v2.0.

<7-1> Animal Test of G-CSF Mutant Protein

Animal test was performed to determine the duration of the CSF mutant protein of the invention and its fusion protein in the body. All the procedures such as purchase, breeding, administration and blood collection of test animals were performed by Qu-BEST Consulting Co., Ltd.

For the test animals, 6-week-old ICR and SPF male mice were purchased from Samtako. The mice were inspected and adapted for at least 6 days. On the last day of the adaptation period, individual weight was measured. Based on the body weight, healthy animals without weight gain and general symptoms were selected and randomly arranged so that the average weight of each group was as equal as possible (35~45 g per animal). Each experimental group was assigned 6 animals.

On the day of the administration of the test sample, a unit dose for each animal was calculated (5 mL/kg) based on the body weight measured immediately before the administration. The G-CSF mutant protein (20 µg/kg) or the G-CSF mutant transferrin fusion protein (100 µg/kg) was slowly injected into the Intravenous Bolus by using a disposable syringe (1 mL, 26G needle). The day of administration was defined as day 1 of the test.

After the injection, blood was drawn from the animals by orbital collection at the time point of 0.25, 0.5, 1, 3, 6, 12, 24, 48, and 72 hours respectively. The blood sample was centrifuged at 10,000~13,000 rpm for 1~2 minutes to separate plasma. The separated plasma was loaded in a tube (about 50 µL/tube) attached with a label containing the information of test type, animal number, and sampling time. The tube was stored in a deep freezer (approximately −70° C.) until the day of analysis.

<7-2> Mouse Pharmacokinetics of G-CSF Mutant Proteins

The amount of active G-CSF in plasma was determined by ELISA after thawing the sample on ice. The quantification of G-CSF in plasma by ELISA was performed by using Human G-CSF ELISA Kit, pink-ONE (Koma Biotech.) according to the manual of the reagent. The calibration curve of the absorbance according to the protein concentration to the standard solution was prepared and the G-CSF mutant content in the test solution was determined by regression analysis Non-compartmental pharmacokinetic analysis was performed from the mean concentration-time profile of each test compound by applying IV Bolus non-compartment analysis input to PKsolver v2.0 program. The pharmacokinetic parameters evaluate the terminal half-life ($t_{1/2}$).

The half-life of proteins in plasma is shown in FIG. 11. As shown in FIG. 11, G-CSF(T116C) mutant protein displayed a blood half-life similar to that of natural human G-CSF. This is a result of similar filtration rate in the kidney, since the G-CSF(T116C) mutant protein has a similar protein radius to the G-CSF. G-CSF-Tf protein showed an improved blood half-life compared to G-CSF. This is because the fusion of transferrin to the G-CSF protein results in a significant increase in the protein radius, resulting in a significantly lower renal filtration rate. The G-CSF(T116C)-Tf fusion protein in which G-CSF(T116C) was fused to transferrin showed more extended half-life than that of G-CSF-Tf but displayed similar half-life to that of PEGylated G-CSF. Therefore, it was suggested that when the G-CSF(T116C) mutant protein having the increased resistance against blood protease was fused to transferrin, the renal filtration rate was decreased and the blood stability was improved, resulting in the maximization of in vivo blood half-life (FIG. 11).

Example 8: Pharmacodynamics of G-CSF Mutant Proteins in Leukopenia Rats

To obtain the pharmacokinetic indices of the proteins of the present invention, hematologic analysis was performed using a rat disease model (Neutropenic Rat). All the procedures such as purchase, breeding, administration and hematologic analysis of test animals were performed by Qu-BEST Consulting Co., Ltd. The hematologic analysis items include WBC, NEU, RBC, HGB, HCT, MCV, MCH, MCHC, PLT, and Differential leucocyte count, etc.

5-week-old SPF Sprague Dawley male rats were adapted at least 5 days and then randomly allocated into four groups. Each rat was in the weight range of 350~400 g. One day before the administration of the test sample, cyclophosphamide (90 mg/kg) was intraperitoneally administered once to induce leukopenia (Neutropenic). The SD rats were intravenously administered with G-CSF once, followed by hematologic tests for 5 days. The test compound was diluted in PBS (Phosphate Buffered Saline) to make the final concentration of 0.004 mg/mL. On the day of the administration of the test sample, a unit dose for each animal was calculated (2 mL/kg) based on the body weight measured immediately before the administration. The test sample was slowly injected into the Intravenous Bolus by using a disposable syringe (1 mL, 26G needle). The day of administration was defined as day 1 of the test.

Before the administration and 6, 12, 24, 48, and 72 hours after the administration, blood collection (approximately 200 μl) was performed in the jugular vein using a disposable syringe (1 mL, 26G needle). The blood was stored in the tube treated with an anticoagulant (5% sodium EDTA) to prevent the blood from coagulation. The components in the blood were analyzed using an automatic blood analyzer in a refrigerated state within 3 hours. The results are presented with mean value and standard deviation. The difference between the control and each experimental group was compared statistically by using GraphPad Prism by One-way ANOVA and Dunnett's test.

Time-dependent neutrophil levels after the administration of G-CSF-Tf and its mutant proteins were presented in FIG. 2. As shown in FIG. 12, from the comparison of the neutrophil levels among the test samples, it was confirmed that the G-CSF(T116C)-Tf administered group displayed higher absolute neutrophil count than the G-CSF and PEGylated G-CSF administered groups after 6 and 12 hours from the administration. The absolute neutrophil count of G-CSF was a little higher than that of the control 24 hours after the administration, which was though not significant. In the meantime, PEGylated G-CSF and G-cSF(T116C)-Tf displayed the increased WBC (white blood cell) and neutrophil levels in the rats having leukopenia induced by cyclophosphamide up to 24 hours from the administration. G-CSF (T116C)-Tf fusion protein was circulated in vivo by using transferrin as a mediator, during which in vivo activity was maintained longer than G-CSF and was as high as that of PEGylated G-CSF. On the other hand, the pharmacokinetic parameters (Cmax and AUC0-t) of the fusion protein were higher than those of G-CSF, as shown in FIG. 9. This seemed to be because the neutrophilic precursor cell proliferation was greater in the protein than in PEGylated G-CSF in the same length of period (FIG. 12).

INDUSTRIAL APPLICABILITY

The induced material in this invention exhibits G-CSF like biological activity that has been used clinically, so that the material of the present invention can be used for the treatment of ischemic disease or as an anticancer adjuvant for the prevention of infectious complications caused by neutropenia resulted from chemo-therapy or radio-therapy for the treatment of cancer due to its activity of stimulating neutrophil granulopoiesis.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A fusion protein in which transferrin is peptide-bonded to a G-CSF (granulocyte-colony stimulating factor) mutant protein in which the 116th threonine is substituted with a cysteine.

2. The fusion protein according to claim 1, wherein the transferrin has the deletion of a signal peptide at the amino terminal region.

3. A method, comprising administering the fusion protein of claim 2 to a subject.

4. The fusion protein according to claim 1, wherein the substituted cysteine forms a disulfide bond with the 17th cysteine of the G-CSF mutant protein.

5. A method, comprising administering the fusion protein of claim 4 to a subject.

6. A method, comprising administering the fusion protein of claim 1 to a subject.

7. A fusion protein, comprising a transferrin protein that is peptide-bonded to a G-CSF (granulocyte-colony stimulating factor) mutant protein in which the 116th threonine is a substituted with a cysteine.

8. The fusion protein according to claim 7, wherein the transferrin protein does not have a native signal peptide at the amino terminal region.

9. A method, comprising administering the fusion protein of claim 7 to a subject.

10. A fusion protein, comprising: a G-CSF (granulocyte-colony stimulating factor) mutant protein in which the 116th threonin is substituted with a cysteine; and
   a transferrin protein peptide-bonded to the G-CSF mutant protein, wherein the transferrin has deletion of a signal peptide at the amino terminal region.

11. A method, comprising administering the fusion protein of claim 10 to a subject.

* * * * *